(12) United States Patent
Shugrue et al.

(10) Patent No.: US 8,568,424 B2
(45) Date of Patent: Oct. 29, 2013

(54) HYSTEROSCOPIC TISSUE REMOVAL SYSTEM WITH IMPROVED FLUID MANAGEMENT AND/OR MONITORING CAPABILITIES

(75) Inventors: Nicole Marie Shugrue, Franklin, MA (US); Ronald David Adams, Holliston, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 13/341,136

(22) Filed: Dec. 30, 2011

(65) Prior Publication Data

US 2012/0172888 A1  Jul. 5, 2012

Related U.S. Application Data

(60) Provisional application No. 61/428,713, filed on Dec. 30, 2010.

(51) Int. Cl.
*A61B 17/42*  (2006.01)
(52) U.S. Cl.
USPC ......................................... 606/119
(58) Field of Classification Search
USPC ......... 606/119, 120, 125–128, 167, 170–171, 606/174, 180; 604/19, 22, 27, 30–35, 604/40–45, 65–67, 118–121, 503, 604/540–543; 600/560–568
See application file for complete search history.

(56) References Cited

U.S. PATENT DOCUMENTS

| | | | |
|---|---|---|---|
| 5,213,571 A * | 5/1993 | Fujio et al. | 604/31 |
| 5,643,302 A * | 7/1997 | Beiser et al. | 606/167 |
| 5,643,304 A | 7/1997 | Schechter et al. | |
| 5,685,840 A * | 11/1997 | Schechter et al. | 604/22 |
| 5,730,752 A | 3/1998 | Alden et al. | |
| 6,032,673 A | 3/2000 | Savage et al. | |
| 6,159,160 A * | 12/2000 | Hsei et al. | 600/560 |

(Continued)

FOREIGN PATENT DOCUMENTS

WO  WO 99/11184 A1  3/1999

OTHER PUBLICATIONS

PCT International Search Report for PCT/US2011/068092, Applicant: Hologic, Inc., Form PCT/ISA/210 and 220, dated May 15, 2012 (9pages).

(Continued)

*Primary Examiner* — Ryan Severson
*Assistant Examiner* — David Eastwood
(74) *Attorney, Agent, or Firm* — Vista IP Law Group LLP

(57) ABSTRACT

A hysteroscopic tissue removal system having improved fluid management and/or monitoring capabilities. According to one embodiment, the system includes a hysteroscope and a tissue removal device, the tissue removal device being selectively operable and being removably mounted in an operating channel of the hysteroscope. The system also includes a fluid source and a fluid pump, the fluid pump being coupled to the fluid source and to a fluid input channel of the hysteroscope so as to pump fluid from the fluid source to the fluid input channel, the fluid pump being selectively operable. The system further includes a selectively operable switch, coupled to both the tissue removal device and the fluid pump, for actuating both the tissue removal device and the pump. If desired, a delay mechanism may be interposed between the switch and the tissue removal device to delay operation of the tissue removal device relative to the pump.

13 Claims, 16 Drawing Sheets

(56) References Cited

U.S. PATENT DOCUMENTS

| | | | |
|---|---|---|---|
| 6,396,583 B1* | 5/2002 | Clare | 356/436 |
| 7,204,821 B1* | 4/2007 | Clare et al. | 604/30 |
| 7,226,459 B2 | 6/2007 | Cesarini et al. | |
| 8,206,342 B2 | 6/2012 | Hacker et al. | |
| 2004/0215099 A1* | 10/2004 | Sampson et al. | 600/560 |
| 2006/0047185 A1* | 3/2006 | Shener et al. | 600/156 |
| 2008/0091061 A1* | 4/2008 | Kumar et al. | 600/104 |
| 2009/0270898 A1 | 10/2009 | Chin et al. | |

OTHER PUBLICATIONS

PCT Written Opinion of the International Search Authority for PCT/US2011/068092, Applicant: Hologic, Inc., Form PCT/ISA/237, dated May 15, 2012 (7pages).

* cited by examiner

HYSTEROSCOPIC TISSUE REMOVAL SYSTEM WITH IMPROVED FLUID MANAGEMENT AND/OR MONITORING CAPABILITIES

RELATED APPLICATION DATA

The present application claims the benefit under 35 U.S.C. §119 to U.S. provisional application No. 61/428,713, filed Dec. 30, 2010, the contents of which are fully incorporated herein by reference.

BACKGROUND

1. Field

The present inventions relate generally to hysteroscopic tissue removal systems for the removal of uterine fibroids and other abnormal gynecological tissues and relate more particularly to a novel hysteroscopic tissue removal system having improved fluid management and/or monitoring capabilities.

2. Description of the Related Art

It is believed that uterine fibroids occur in a substantial percentage of the female population, perhaps in at least 20 to 40 percent of all women. Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction.

Current treatments for uterine fibroids include pharmacological therapy, hysterectomy, uterine artery embolization, and hysteroscopic resection. Pharmacological therapy typically involves the administration of NSAIDS (non-steroidal anti-inflammatory drugs), estrogen-progesterone combinations, and GnRH (gonadotropin releasing hormone) analogues. However, current pharmacological therapies are largely ineffective and merely palliative.

By comparison, a hysterectomy involves the surgical removal of the uterus from a patient. For this reason, a hysterectomy represents a highly effective way of ridding a patient of uterine fibroids. As a result, several hundred thousand hysterectomies are typically performed annually in the United States to treat uterine fibroids. However, despite their widespread use, hysterectomies also possess certain disadvantages, such as a loss of fertility, sexual dysfunction, and the risks commonly associated with a major surgical procedure, such as hemorrhaging, lesions, infections, pain and prolonged recovery.

Uterine artery embolization involves inserting a catheter into a femoral artery and then guiding the catheter to a uterine fibroid artery. Small particles are then injected from the catheter into the fibroid artery, blocking its blood supply and causing it to eventually shrink and die. Although this procedure is less invasive than a hysterectomy, it often results in pain-related, post-surgical complications. Moreover, the physicians that are trained to perform uterine artery embolization are typically interventional radiologists, as opposed to physicians trained specifically to take care of gynecological problems, whereas the physicians trained specifically to take care of gynecological problems typically do not possess the skill to perform catheter-based uterine artery embolization.

Hysteroscopic resection typically involves inserting a hysteroscope, i.e., an imaging scope, into the uterus transcervically through the vagina and then cutting away the fibroid from the uterus using a device delivered to the fibroid by the hysteroscope. Hysteroscopic resections typically fall into one of two varieties. In one variety, an electrocautery device in the form of a loop-shaped cutting wire is fixedly mounted on the distal end of the hysteroscope—the combination of the hysteroscope and the electrocautery device typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906,615, inventor Thompson, issued May 25, 1999.

In the other variety of hysteroscopic resection, an electromechanical cutter is inserted through a working channel in the hysteroscope. Tissue is then removed by contacting the cutter, which typically has a rotating cutting instrument, with the part of the uterus wall of interest. Examples of the electromechanical cutter variety of hysteroscopic resection are disclosed in, for example, U.S. Pat. No. 7,226,459, inventors Cesarini et al., issued Jun. 5, 2007; U.S. Pat. No. 6,032,673, inventors Savage et al., issued Mar. 7, 2000; U.S. Pat. No. 5,730,752, inventors Alden et al., issued Mar. 24, 1998; U.S. Patent Application Publication No. US 2009/0270898 A1, inventors Chin et al., published Oct. 29, 2009; U.S. Patent Application Publication No. US 2006/0047185 A1, inventors Shener et al., published Mar. 2, 2006; and PCT International Publication No. WO 99/11184, published Mar. 11, 1999, all of which are incorporated herein by reference.

In the above-described varieties of hysteroscopic resection, prior to fibroid removal, the uterus is typically distended to create a working space within the uterus. Such a working space does not normally exist naturally in the uterus because the uterus is a flaccid organ with its walls typically in contact with one another when in a relaxed state. The conventional technique for creating such a working space within the uterus is to administer a fluid to the uterus through the hysteroscope under sufficient pressure to cause the uterus to become distended.

A benefit of the fluid distension is the tamponade effect that the distension fluid provides on resected vascular tissue. Since the distension fluid is typically maintained at a pressure that exceeds the patient's mean arterial pressure (MAP), the fluid pressure provided by the distension fluid prevents the leakage of arterial blood from the resected tissue from flowing or oozing into the uterine cavity. When arterial blood flows or oozes into the cavity, it mixes with the distension fluid and renders visualization more difficult and, if not constrained, the flowing or oozing blood will force the suspension of the procedure. Thus, maintenance of fluid pressure above the intracavity arterial pressure is highly beneficial for the maintenance of a clear visual field.

Examples of the fluid used conventionally to distend the uterus include gases like carbon dioxide or, more commonly, liquids like water or certain aqueous solutions, e.g., a saline or other physiologic solution or a sugar-based or other non-physiologic solution. Because the distending fluid is administered under pressure, which pressure may be as great as 100 mm Hg or greater, there is a risk, especially when vascular tissue is cut, that the distending fluid may be taken up by a blood vessel in the uterus, i.e., intravasation, which uptake may be harmful to the patient. Thus, it is customary to monitor the fluid uptake on a continuous basis using a scale system.

Despite the risks of intravasation, with proper monitoring of fluid uptake, hysteroscopic resection is a highly effective and safe technique for removing uterine fibroids. One shortcoming that has been noted by the present inventors in connection with existing hysteroscopic tissue removal systems, particularly of the electromechanical cutter variety, is that it is often difficult to maintain fluid distension of the uterus during the resection procedure. This is because, during the resection procedure, suction is typically applied to the electromechanical cutter device to draw tissue into the device and to facilitate the removal of the resected tissue from the uterus. However, such suction also typically has the effect of removing some of the distending fluid from the uterus along with the resected tissue. While most systems typically have a pressure sensor that actuates a pump to deliver replacement distending fluid to the uterus when the fluid pressure in the uterus drops due to the loss of distending fluid, the drop in pressure may be precipitous, particularly if a high suction pressure is applied. A steep drop in uterine fluid pressure will result in the leakage of blood into the uterine cavity, causing a loss of visualization and ultimately stoppage of the procedure if the surgeon can no longer properly visualize the treatment site. Moreover, depending on the extent and speed of the drop in uterine fluid pressure, there may be a significant lapse of time before the uterine fluid pressure can be restored to a desired level such that adequate visualization is possible. Such lapses in time are clearly undesirable as they interrupt the resection procedure, as well as lengthen the overall time for the procedure and increase the risk of intravasation.

SUMMARY OF THE INVENTION

The presently disclosed inventions are directed to hysteroscopic tissue removal systems that may be used, without limitation, for removing uterine fibroids and other gynecological tissues.

The hysteroscopic tissue removal systems disclosed herein may possess improved fluid management and/or monitoring capabilities, especially as compared to existing hysteroscopic tissue removal systems. For example, embodiments of the disclosed hysteroscopic tissue removal systems may be provided with a shared switch to actuate both the operation of a tissue removal device, preferably of the electromechanical cutter variety, and the operation of a fluid pump used to supply distending fluid to the patient. In this manner, the net loss of distending fluid from the uterus following actuation of the tissue removal device may be minimized. If desired, a delay mechanism may be interposed between the shared switch and the tissue removal device to delay actuation of the tissue removal device, relative to actuation of the pump, by a desired time interval. Therefore, a hysteroscopic tissue removal system provided in accordance with some embodiments may comprise (a) a hysteroscope; (b) a tissue removal device, said tissue removal device being selectively operable and being removably mounted in an operating channel of said hysteroscope; (c) a fluid source; (d) a fluid pump, said fluid pump being coupled to said fluid source and to a fluid input channel of said hysteroscope so as to pump fluid from said fluid source to said fluid input channel, said fluid pump being selectively operable; and (e) a selectively operable switch, coupled to both said tissue removal device and said fluid pump, for actuating both said tissue removal device and said fluid pump.

As another example of the improved fluid management and/or monitoring capabilities of the disclosed hysteroscopic tissue removal systems, especially as compared to existing hysteroscopic tissue removal systems, a fluid deficit display may be provided that is easily viewable by a doctor while the doctor is performing a hysteroscope-assisted medical procedure on a patient. For purposes of the present specification and claims, the term "fluid deficit" represents the volume of fluid taken up by a patient over a period of time and is determined by calculating the difference between the volume of fluid introduced into a patient over the period of time minus the volume of fluid collected from the patient during the same period of time. The fluid deficit display may be attached to the aforementioned viewing monitor so that the doctor can view the fluid deficit display without turning away from the monitor that is showing the procedure. Such an arrangement is advantageous over that found in existing systems, wherein instrumentation for determining a fluid deficit is positioned behind or to the side of the doctor and the fluid deficit display is located on or near said fluid deficit determining instrumentation. In some embodiments, the fluid deficit determining instrumentation may continue to be positioned behind or to the side of the doctor, with the fluid deficit display being positioned in front of the doctor and being positioned sufficiently close to the monitor used to view the medical procedure so that the doctor can view the display without turning away from the monitor. To eliminate the need for wires connecting the fluid deficit display and the fluid deficit determining instrumentation, the fluid deficit display of the present inventions may be wirelessly connected to the fluid deficit determining instrumentation.

Therefore, a hysteroscopic tissue removal system provided in accordance with some embodiments may comprise (a) a hysteroscope, the hysteroscope being removably insertable into a patient; (b) a light source optically coupled to an illumination channel of said hysteroscope; (c) a camera optically coupled to a viewing channel of said hysteroscope; (d) a monitor coupled to said camera for displaying images collected by said camera; (e) a tissue removal device, said tissue removal device being removably mounted in an operating channel of said hysteroscope; (f) means for determining, in real-time, a current fluid deficit for the patient; (g) a display for displaying the current fluid deficit; and (h) means for securing said display proximate to said monitor. The hysteroscopic tissue removal system may further comprise means for wirelessly coupling said determining means and said display so as to enable wireless communication of the current fluid deficit from said determining means to said display.

As yet another example of the improved fluid management and/or monitoring capabilities of the disclosed hysteroscopic tissue removal systems, especially as compared to existing hysteroscopic tissue removal systems, the hysteroscopic tissue removal system may further include a plurality of independently-controllable vacuum sources. In some embodiments, a first such vacuum source may be coupled to a tissue removal device, particularly a tissue removal device of the electromechanical cutter variety, and a second such vacuum source may be coupled to a patient drape used to collect distending fluid leaking from the patient so that said fluid may be accounted for when determining the current fluid deficit. Because the first and second vacuum sources are independently controllable, the first such vacuum source may be operated at a comparatively high pressure, which may be desirable in order to optimize performance of the tissue removal device. By contrast, the second such vacuum source may be operated at a comparatively low pressure, which may be desirable, for example, to prevent the drape, when drained, from collapsing onto itself or from making an undesirable whistling sound. Such an arrangement is clearly advantageous over that found in existing systems, wherein the same vacuum source is coupled both to the tissue removal device and to the drape.

Therefore, a hysteroscopic tissue removal system provided in accordance with some embodiments may comprise (a) a hysteroscope, the hysteroscope being removably insertable into a patient; (b) a tissue removal device, said tissue removal device being removably mounted in an operating channel of said hysteroscope; (c) a drape for collecting fluid leaking from the patient; (d) a first vacuum, said first vacuum being operably coupled to said tissue removal device; and (e) a second vacuum, said second vacuum being operably coupled to an outflow port of said drape; (f) wherein said first vacuum and said second vacuum are independently-controllable in terms of suction pressure.

As still another example of the improved fluid management and/or monitoring capabilities of the disclosed hysteroscopic tissue removal systems, especially as compared to existing hysteroscopic tissue removal systems, the hysteroscopic tissue removal system may further include a fluid bag stand that includes means for holding a used fluid bag, in addition to including means for holding two unused, or partially unused, fluid bags. As a result, once a fluid bag has been used, it may be removed from its hook, turned upside-down, and suspended from the stand using a clamp. Since the used bag is still hanging from the stand, the fluid remaining in the bag may be accounted for gravimetrically.

Therefore, an embodiment of a hysteroscopic tissue removal system provided in accordance with some embodiments may comprise (a) a hysteroscope, the hysteroscope being removably insertable into a patient; (b) a tissue removal device, said tissue removal device being removably mounted in an operating channel of said hysteroscope; and (c) a fluid delivery system, said fluid delivery system being coupled to a fluid input channel of said hysteroscope, said fluid delivery system comprising a fluid bag stand, said fluid bag stand comprising means for holding at least one fluid bag in an upright orientation, said fluid bag further comprising a clamp for holding a fluid bag in an inverted orientation, said fluid delivery system further comprising at least one fluid bag suspended on the fluid bag stand. The hysteroscopic tissue removal system can further comprise means for determining the volume of fluid contained in the at least one fluid bag suspended from the fluid bag stand.

As can be appreciated, the fluid bag stand of some embodiments of the present inventions is not limited to use in hysteroscopic tissue removal systems and may be used in other medical applications, such as, but not limited to, intravenous fluid applications.

As a further example of the improved fluid management and/or monitoring capabilities of the disclosed hysteroscopic tissue removal systems, especially as compared to existing hysteroscopic tissue removal systems, the hysteroscopic tissue removal systems may be further provided with a display positioned on the fluid bag stand, the display including, by way of illustration and not limitation, a multicolor digital bar graph meter representing the current fluid deficit as a fraction of a settable fluid deficit limit. For example, a first portion (or "comfortable zone") of a digital bar graph meter may light in a first color to depict a current fluid deficit up to a first threshold defined as "x" percentage of the limit, with a second portion (or "caution zone") of the digital bar graph meter lighting in a second color to depict a current fluid deficit up to a second threshold defined as "x+y" percentage of the limit, and a third portion (or "danger zone") of the digital bar graph meter lighting in a third color to depict a current fluid deficit in excess of the second threshold. The display may further include a numerical read-out of the current deficit display, for example, with the numerical read-out being shown in a color that matches the color of the current fluid deficit as depicted by the multicolor digital bar graph meter.

Additional aspects, features and advantages of the disclosed inventions are set forth in part in the description which follows, and will also in part be apparent from the description or may be learned by practice of the invention. In the description, reference is made to the accompanying drawings which form a part thereof and in which is shown by way of illustration various embodiments for practicing the inventions. Although the embodiments are described in sufficient detail to enable those skilled in the art to practice the disclosed inventions, it is to be understood that other embodiments may be utilized and that structural changes may be made without departing from the scope of the inventions, which are defined by the claims appended hereto. The following detailed description is, therefore, for purposes of illustration, and is not to be taken in a limiting sense.

BRIEF DESCRIPTION OF THE DRAWINGS

The accompanying drawings, which are hereby incorporated into and constitute a part of this specification, illustrate various embodiments of the inventions and, together with the description, serve to explain the principles of the inventions. In the drawings wherein like reference numerals represent like parts.

DETAILED DESCRIPTION OF THE ILLUSTRATED EMBODIMENTS

The illustrated embodiments are described below primarily in the context of devices and procedures optimized for performing one or more therapeutic or diagnostic gynecological or urological procedures such as the removal of uterine fibroids or other abnormal uterine tissue. However, it is to be understood that the illustrated and described devices and related procedures may be used in a wide variety of applications throughout the body, through a variety of access pathways.

For example, the devices of the illustrated and described embodiments may be optimized for use via open surgery, less invasive access such as laparoscopic access, or minimally invasive procedures such as via percutaneous access. In addition, the illustrated and described devices may be configured for access to a therapeutic or diagnostic site via any of the body's natural openings to accomplish access via the ears, nose, mouth, and via trans-rectal, urethral and vaginal approach.

In addition to the performance of one or more gynecological and urologic procedures described in detail herein, the systems, methods, apparatus and devices of the embodiments may be used to perform one or more additional procedures, including but not limited to access and tissue manipulation or removal from any of a variety of organs such as the bladder, breast, lung, stomach, bowel, esophagus, oral cavity, rectum, nasal sinus, Eustachian tubes, heart, gall bladder, arteries, veins, and various ducts. Routes of access include but are not limited to trans-cervical; trans-vaginal-wall; trans-uteral; trans-vesicle; trans-urethral; and other routes.

Figure 1A:
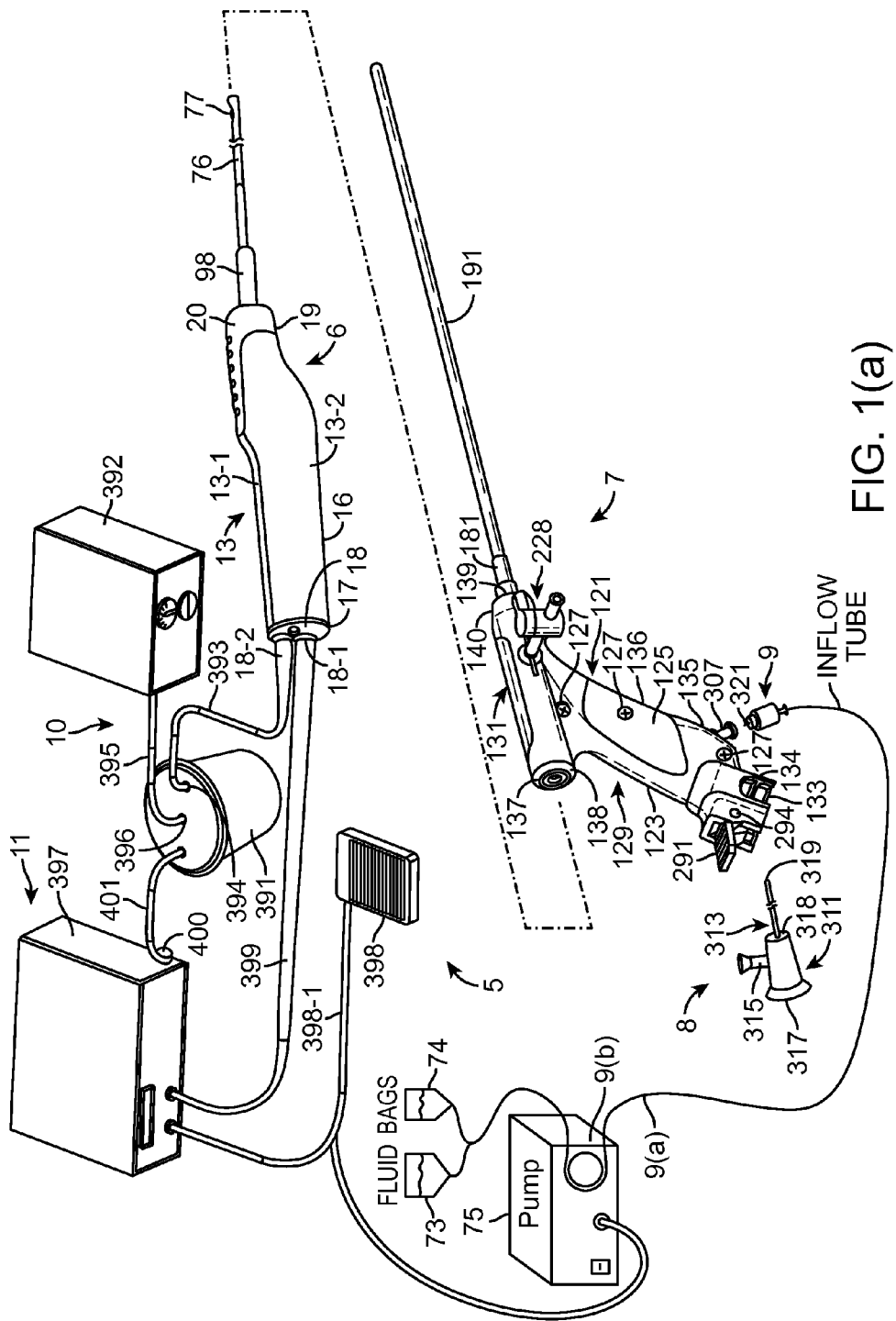
FIG. 1(a) is a perspective view of one embodiment of a hysteroscopic tissue removal system.

FIG. 1(a) depicts an exemplary embodiment of a hysteroscopic tissue removal system 5, which can account for fluid pressure drop and/or the lapse in time by activating a fluid pump assembly 75 simultaneously with the motor drive assembly 11. In this embodiment, when the user activates foot pedal 398 or other activation switch, the fluid pump assembly 75 and the motor drive assembly 11 can be simultaneously activated or substantially simultaneously activated, thereby reducing possible fluid pressure loss at the surgical site and/or limit the lapse of time before the fluid pressure at the surgical site can be restored to the desired fluid pressure level.

In particular, it can be advantageous to activate the fluid pump assembly 75, and activate the motor drive assembly 11 after a period of time has passed. By activating the motor drive assembly 11 after a period of time, the fluid pump assembly 75 can elevate the fluid pressure at the surgical site above the desired fluid level pressure in order to account for a pressure loss induced by activation of the motor drive assembly 11. By activating fluid pump assembly 75 before activating the motor drive assembly 11, the system 5 can also limit the occurrence of significant lapses of time that may be necessary to restore the fluid pressure at the surgical site to the desired level. The time delay between activating the fluid pump assembly 75 and the motor drive assembly 11 can be based on a variety of criteria, including but not limited to a time period threshold and/or a pressure threshold.

By way of non-limited example, the motor drive assembly 11 may be activated after a predetermined period following activation of the fluid pump assembly 75. The predetermined period may be set by a user prior to using the system 5. Alternatively, the predetermined period can be set within the system 5. The predetermined period can be any length of time, for example, 0.1 second, 0.25 second, 0.5 second, 0.75 second, 1 second, 2 seconds, 3 seconds, 4 seconds, 5 seconds, 6 seconds, 7 seconds, or to like. The predetermined time period can range anywhere between 0 seconds and 10 seconds, 0.25 second to 7 seconds, 0.5 second to 5 seconds, 1 second to 3 seconds, or the like.

In one embodiment, the motor drive assembly 11 is activated after the fluid pump assembly 75, when the fluid pressure at the surgical site has achieved a certain fluid pressure threshold level. The fluid pressure threshold level can be an elevated pressure level above the user's desired pressure level at the surgical site. For example, the user can select a desired pressure level of 60 mm Hg, and the system 5 can be configured to elevate the fluid pressure at the surgical site to, for example, 80 mm Hg before activating the motor drive assembly 11. The elevated fluid pressure threshold level can be set by a user or the elevated fluid pressure level threshold can be set within the system 5. The elevated fluid pressure level threshold can be an absolute number (for example, 5 mm Hg, 10 mm Hg, 15 mm Hg, etc.) above the desired fluid pressure level or can be a percentage (for example, 5%, 10%, 15%, etc.) above the desired fluid pressure threshold level.

In one embodiment, the system 5 can be configured to prevent elevation of the fluid pressure level above a maximum pressure level. The maximum pressure level can be set by a user or it can be set within the system 5. The maximum fluid pressure level can be any number, for example, 90 mm Hg, 100 mm Hg, 125 mm Hg, 150 mm Hg, 175 mm Hg, and 200 mm Hg. In an embodiment, the system 5 is configured to prevent elevation of the fluid pressure level above the Food and Drug Administration (FDA) guidelines for maximum sustained pressure. For example, the FDA guidelines currently state that maximum sustained intrauterine pressure should not exceed 150 mm Hg. Further, the FDA guidelines also state that pressure overshoot should not exceed 150 mm Hg for more than 15 seconds during initial distension.

In one embodiment, the system 5 can be configured to activate the motor drive assembly 11 after activation of the fluid pump assembly 75 when a predetermined time period has passed or when an elevated pressure level threshold has been satisfied. It can be advantageous for the system 5 to analyze both a time criteria and an elevated pressure level threshold criteria because the system 5 can ensure that the motor drive assembly 11 is activated within an optimal period of time while also allowing the fluid pressure level at the surgical site to potentially reach an optimal pressure level at the surgical site. The foregoing examples and embodiments are further described below with respect to the remaining figures. An optimal period of time helps ensure that there is not a significant delay from when the user activates the foot pedal 398 to when the motor drive assembly 11 is activated. An optimal pressure level helps ensure that visualization of the surgical site is maintained throughout the surgical procedure.

Referring to FIG. 1(a), there is illustrated a perspective view of one embodiment of a hysteroscopic tissue removal system 5. The system 5 may be used for removing uterine fibroids and other abnormal gynecological tissues. However, it should be understood that system 5 is not limited to such a use and may be used in other anatomies and medical specialties, such as urology and general surgery that may be apparent to those of ordinary skill in the art. System 5 may comprise a tissue removal device 6, an introducer device (or hysteroscope) 7, a fluid supply system 9, a vacuum assembly 10, a fluid pump assembly 75, and a motor drive assembly 11. In an embodiment the introducer device 7 can be inserted into a patient to reach a surgical site. The introducer 7 can be coupled to inflow tubing 9(*a*), which is coupled to the fluid pump assembly 75. The fluid pump assembly 75 can be coupled to fluid bags 73, 74. In use, the fluid pump assembly 75 can be configured to pump inflow fluid from fluid bags 73, 74 into inflow tubing 9(*a*) to inject fluid through the introducer 7 and into the surgical site.

The introducer 7 can also be configured to receive a tissue removal system 6. The tissue removal system 6 can be coupled to a flexible drive cable 399, which can be coupled to a motor drive assembly 11. The motor drive assembly 11 may comprise a motor for driving the flexible drive cable, which can be configured to drive a cutting device within the tissue removal device 6. The tissue removal device 6 can also be coupled to an outflow fluid tube 393, which can be coupled to container 391. Container 391 can be coupled to a vacuum source for pulling fluid from the surgical site through the tissue removal device 6 and into the canisters 391. In an embodiment foot pedal 398 is coupled to the fluid pump assembly 75 and the motor drive assembly 11.

When the user activates the foot pedal 398, the fluid pump assembly 75 and the motor drive assembly 11 can be simultaneously activated. In an embodiment, activation of the foot pedal 398 or other activation switch can activate fluid pump assembly 75 followed by the activation of motor drive assembly 11 after a period of time. Alternatively, when foot pedal 398 is activated, the system can be configured to activate fluid pump assembly 75 followed by the activation of motor drive assembly 11 after the pressure at the surgical site reaches a certain fluid pressure threshold level. In an embodiment, the system can be configured to activate fluid pump assembly 75, and then analyze the time period criteria and the pressure threshold criteria to determine whether either has been satisfied. If the fluid pump assembly 75 has been activated for a predetermined period of time, or if the fluid pressure level at the surgical site has reached a predetermined threshold level, then the system can be configured to activate the motor drive assembly 11.

In one embodiment, it can be advantageous to activate the fluid pump assembly 75 followed by activation of the motor drive assembly 11. As discussed above, activation of the tissue removal device 6 can cause the removal of some of the distension fluid found in the surgical site, thereby causing a drop in fluid pressure at the surgical site. The drop in fluid pressure can be significant, and can destabilize the surgical site, making it difficult for the surgeon to proceed with this procedure. A drop in fluid pressure can result in the leakage of blood into the surgical site, causing a loss of visualization and/or a collapse of the surgical site. Either event can cause the stoppage of the surgical procedure and/or increase the time needed to complete the procedure.

By activating the fluid pump assembly 75, and delaying the activation of the motor drive assembly 11, the system 5 can be configured to raise the fluid pressure at the surgical site to a certain threshold level, thereby compensating for any fluid pressure loss by the subsequent activation of the motor drive assembly 11. In one embodiment, the fluid pump assembly 75 is activated for a period of time in order to elevate the fluid pressure at the surgical site, at which time the motor drive assembly 11 can be activated. The fluid pump assembly 75 can also be activated until a fluid pressure threshold is met at the surgical site, at which time the motor drive assembly 11 can be activated.

In one embodiment, the system 5 can be configured to activate the fluid pump assembly 75 for a period of time or until a threshold fluid pressure is met. After either of the two criteria is satisfied, the system 5 can be configured to activate the motor drive assembly 11. The two criteria embodiment can be advantageous in order to avoid a significant delay between activating the foot pedal 398 and the motor drive assembly 11. A significant delay between the activation of the foot pedal 398 and the motor drive assembly 11 can cause a disruption to the surgical procedure because the surgeon may interpret the delay as a clog in the system or other system malfunction. In some embodiments, the motor drive assembly 11 is activated based on a combination of lapsed time and pressure, for example, after a predetermined pressure is reached and maintained for a pre-determined time period.

In one embodiment, the system 5 may be configured to activate the fluid pump assembly 75 until both the time criteria and pressure criteria are met. After a predetermined amount of time has passed and a predetermined pressure within the body cavity is reached, the system 5 may be configured to activate the motor drive assembly 11. That is, the delay between actuating the fluid pump assembly 75 and actuating the motor drive assembly 11 is based upon both a time period threshold and a pressure threshold.

Figure 1B:
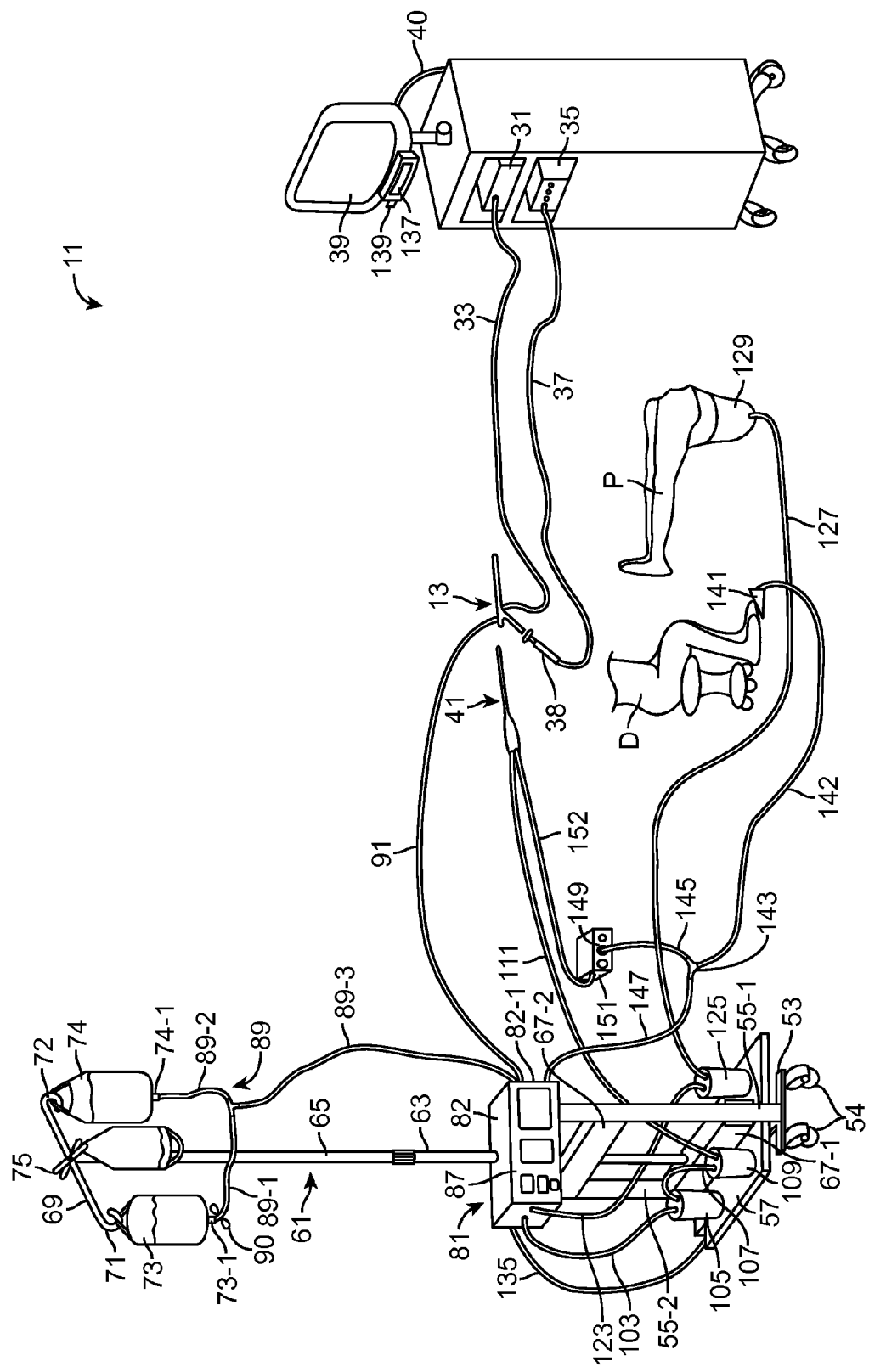
FIG. 1(b) is a perspective view of one embodiment of a hysteroscopic tissue removal system with a doctor and a patient being fragmentarily shown with the system to illustrate how a doctor and a patient may be positioned relative to the system.

Referring now to FIG. 1(*b*), there is shown a perspective view of one embodiment of a hysteroscopic tissue removal system, the hysteroscopic tissue removal system being constructed according to the teachings of the present invention and being represented generally by reference numeral 11. For illustrative purposes, a doctor D and a patient P are fragmentarily depicted to show how system 11 may be positioned during use relative to these individuals. System 11 is particularly well-suited for removing uterine fibroids and other abnormal gynecological tissues. However, it should be understood that system 11 is not limited to such a use and may be used in other anatomies that may be apparent to those of ordinary skill in the art.

Figure 2A:
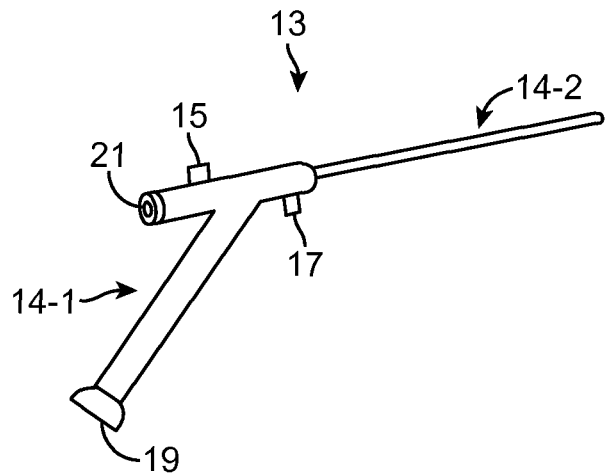
FIGS. 2(a) and 2(b) are enlarged perspective and enlarged transverse section views, respectively, of the hysteroscope shown in FIG. 1, the hysteroscope of FIG. 2(b) being shown with a tissue removal device inserted thereinto.
Figure 2B:
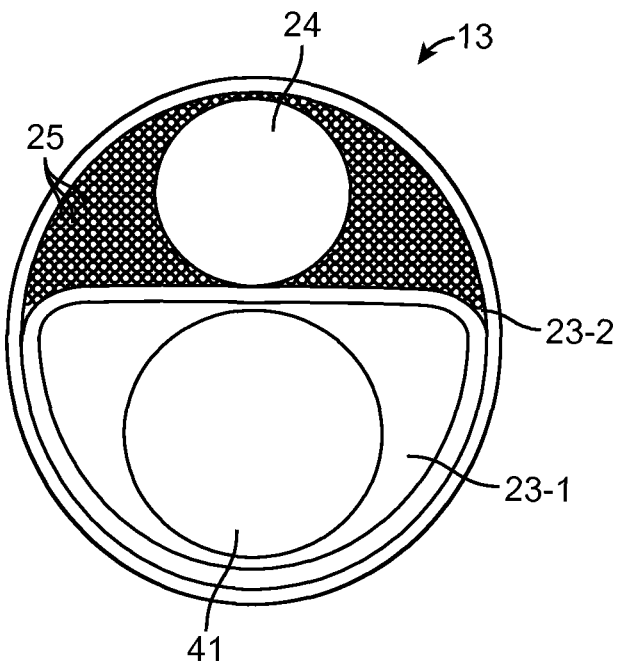

System 11 may comprise a hysteroscope 13, which may be conventional in construction. Hysteroscope 13, which is also shown in FIGS. 2(*a*) and 2(*b*), may be shaped to comprise a handle 14-1, which is adapted to be held in the hand of a user, and a shaft 14-2, which extends distally from handle 14-1 and whose distal end is adapted to be removably inserted into a patient. Handle 14-1 may be shaped to include a fluid input port 15, an illumination input port 17, an observation output port 19, and an instrument input opening 21. In addition, hysteroscope 13 may comprise a plurality of channels extending distally from handle 14-1 and continuing longitudinally through shaft 14-2. Said channels may comprise a first channel 23-1 and a second channel 23-2. First channel 23-1 may be in fluid communication with fluid input port 15 and, at the same time, may be accessible through instrument input opening 21. In this manner, a medical instrument, such as a tissue removal device 41, may be inserted into opening 21 and through first channel 23-1, with the unoccupied remainder of first channel 23-1 being available to conduct distension fluid. A rod lens 24 or other suitable light collecting means may be disposed in second channel 23-2, with the remainder of second channel 23-2 being occupied by fiber optics 25 or other suitable light transmitting means.

System 11 may also comprise a mechanism for supplying the proximal end of fiber optics 25 with illuminating light. In the illustrated embodiment, the illumination supplying mechanism may comprise a light source 31 and an optical cable 33. Cable 33 may comprise a first end optically coupled to light source 31 and an opposite end optically coupled to illumination input port 17 of hysteroscope 13.

System 11 may additionally comprise a mechanism for converting light signals transmitted from rod lens 24 in hysteroscope 13 into corresponding electrical signals. In the illustrated embodiment, the signal converting mechanism may comprise a camera 35 and an optical cable 37. Optical cable 37 may comprise a first end optically coupled to observation output port 19 of hysteroscope 13 through an adapter 38 and a second end optically coupled to camera 35.

System 11 may further comprise a monitor 39, electrically coupled to camera 35 via a cable 40, for converting the electrical signals generated by camera 35 into images. In this manner, monitor 39 may be used to display real-time images of the uterus or other body part into which hysteroscope 13 has been inserted.

Figure 3A:
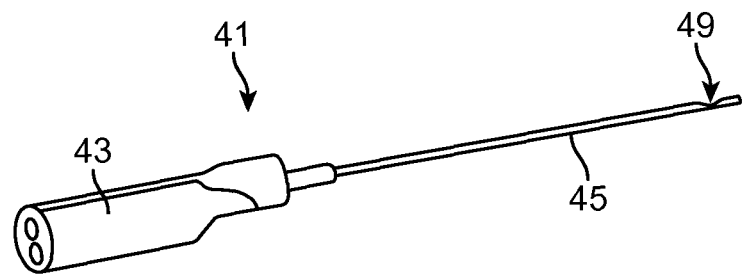
FIGS. 3(a) and 3(b) are enlarged perspective and enlarged fragmentary longitudinal section views, respectively, of the tissue removal device shown in FIG. 1.
Figure 3B:
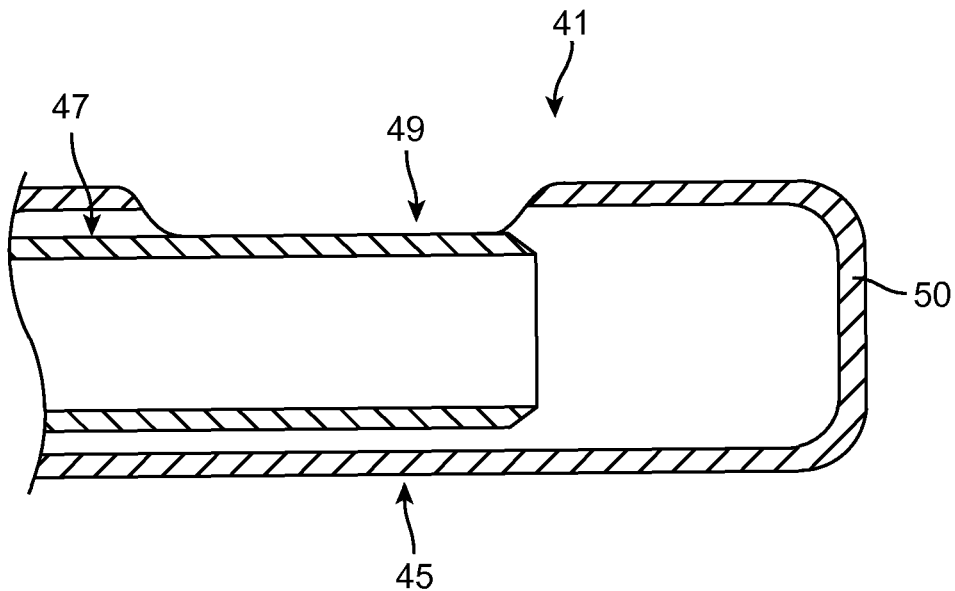

System 11 may further comprise a tissue removal device 41. Tissue removal device 41 may be a tissue removal device of the electromechanical cutter variety, and, more specifically, may be the tissue removal device disclosed in U.S. Patent Application Publication No. US 2009/0270898 A1, inventors Chin et al., published Oct. 29, 2009, which is incorporated herein by reference. Consequently, because device 41 may be identical to the device of the aforementioned published patent application, all of the details of device 41 are not repeated herein and, instead, only certain components of interest are discussed herein. For example, device 41, which is also shown separately in FIGS. 3(a) and 3(b), may comprise a housing 43 ergonomically shaped to fit comfortably in the hand of a user. In addition, device 41 may also comprise an electromechanical cutting mechanism comprising an outer tubular member 45 and an inner tubular member 47, inner tubular member 47 moving rotationally and, at the same time, oscillating translationally relative to outer tubular member 45. Outer tubular member 45 may be shaped to include a resection window 49 into which tissue may be captured and drawn, window 49 being located a short distance, for example, 0.25 inch from a distal end 50 of outer tubular member 45.

Hysteroscope 13 and tissue removal device 41 may be appropriately dimensioned so that outer tubular member 45 of device 41 may be introduced into channel 23-1 of hysteroscope 13 via instrument input opening 21, with the distal end of outer tubular member 45 extending beyond the distal end of shaft 14-2 by a sufficient length to permit resection window 49 to be brought into proximity of the tissue to be cut.

System 11 may further comprise a fluid management and monitoring system. In the illustrated embodiment, the fluid management and monitoring system may comprise a horizontal base 53 having a plurality of casters 54 secured thereto to enable base 53 to be rolled on a floor or similar surface. In addition, said fluid management and monitoring system may also comprise a pair of support beams 55-1 and 55-2 extending vertically upwardly from opposite ends of base 53.

The fluid management and monitoring system may additionally comprise a gravimetric scale 57 positioned over base 53 and between support beams 55-1 and 55-2. As will be explained below in further detail, scale 57 may be used in the determination of a current fluid deficit for a patient.

The fluid management and monitoring system may further comprise a fluid stand 61. Existing fluid bag stands (often referred to as "IV stands") typically have hooks or similar means for suspending two unused, or partially unused, fluid bags. In use, the two fluid bags are suspended on the hooks or similar means and are then typically coupled to a fluid pump using a Y-tubing set, with each of the branched ends of the Y-tubing set being connected to a different one of the two fluid bags and with the unbranched end of the Y-tubing set being connected to the fluid pump. Typically, one of the bags is clamped shut so as not to empty into the Y-tubing set until the other bag has been used; after the first bag has been used, the clamp is then switched to allow the unused bag to pass fluid. One must be careful to ensure that the first-emptying fluid bag does not empty completely before switching to the other fluid bag since this could introduce air into the Y-tubing set, which, in turn, could cause an air embolism or other undesired effect in the patient. Depending on the particular circumstances of the procedure being performed, there may be a need for a third fluid bag. However, one cannot simply remove one of the two used bags from the stand and replace it with an unused or partially used bag since the fluid remaining in the used bags must be accounted for in order to accurately determine the current fluid deficit. Typically, the fluid bag stand has some gravimetric mechanism for determining the mass of fluid in the suspended fluid bags. Therefore, by measuring the mass of the fluid remaining in the bags and taking into account the density of the fluid, one can determine the volume of fluid remaining in the bags. This problem is addressed by the fluid bag stand of the present invention, which includes a clamp or similar mechanism for holding an inverted used bag.

Stand 61 may extend vertically and may comprise a lower pole 63 and an upper pole 65. Lower pole 63 may have its lower end seated on scale 57 and may be stabilized thereon using a pair of supports 67-1 and 67-2, with lower pole 63 being received in supports 67-1 and 67-2 and with supports 67-1 and 67-2 being slidably mounted on beams 55-1 and 55-2. Upper pole 65 may be telescopically received in lower pole 63 so that the height of fluid stand 61 may be adjusted when desired. Stand 61 may additionally comprise a transverse bar 69 fixedly secured to a top end of upper pole 65. Transverse bar 69 may comprise a pair of hooks 71 and 72. Hook 71 may be used to suspend a conventional fluid bag 73 (which may contain a saline or other physiologic solution or may contain a sugar-based or other non-physiologic solution) so that the fluid bag 73 may be drained through a bottom port 73-1 in the conventional fashion, and hook 72 may be used to suspend a conventional fluid bag 74, which may contain a saline or other physiologic solution or may contain a sugar-based or other non-physiologic solution, so that the fluid bag 74 may be drained through a bottom port 74-1 in the conventional fashion.

Figure 4:
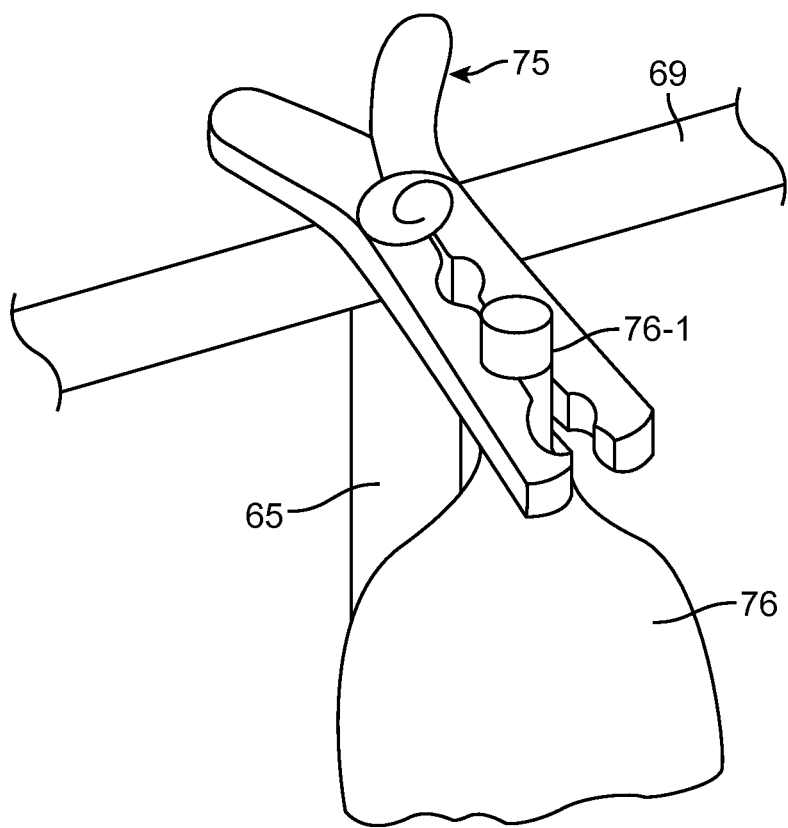
FIG. 4 is an enlarged fragmentary perspective view of the fluid stand shown in FIG. 1, showing the spring-loaded clamp being used to hold a fluid bag in an upside-down orientation.
Figure 6:
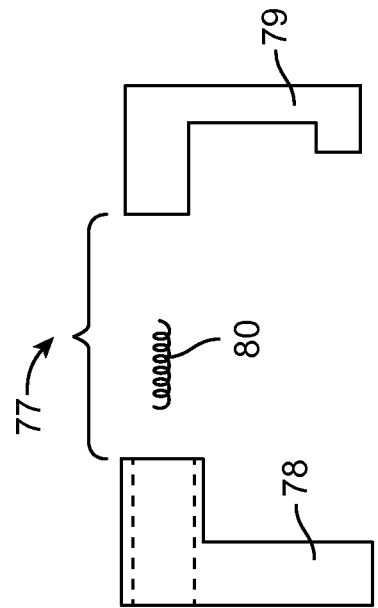
FIG. 6 is a top exploded view of the spring-loaded clamp shown in FIG. 5.
Figure 5:
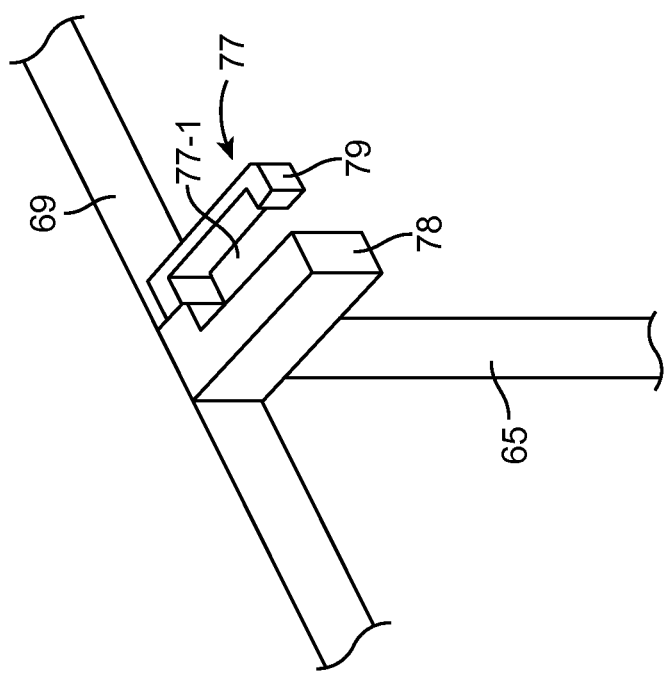
FIG. 5 is an enlarged fragmentary perspective view of an alternate embodiment of a fluid stand to the fluid stand of FIG. 4, the alternate embodiment comprising a different type of spring-loaded clamp.

The fluid stand 61 may also comprise a spring-loaded clamp 75, also shown in FIG. 4, fixedly coupled to transverse bar 69, clamp 75 being adapted to hold a conventional fluid bag 76, which may contain a saline or other physiologic solution or may contain a sugar-based or other non-physiologic solution, in an upside-down orientation by gripping the bottom port 76-1 of fluid bag 76. Clamp 75 may have a clothespin-type construction. Alternatively, another embodiment of a clamp is shown in FIGS. 5 and 6 and is represented generally therein by reference numeral 77. Clamp 77 may comprise a pair of angled members 78 and 79 biased towards one another using a spring 80 to form a generally rectangular slot 77-1.

Figure 7A:
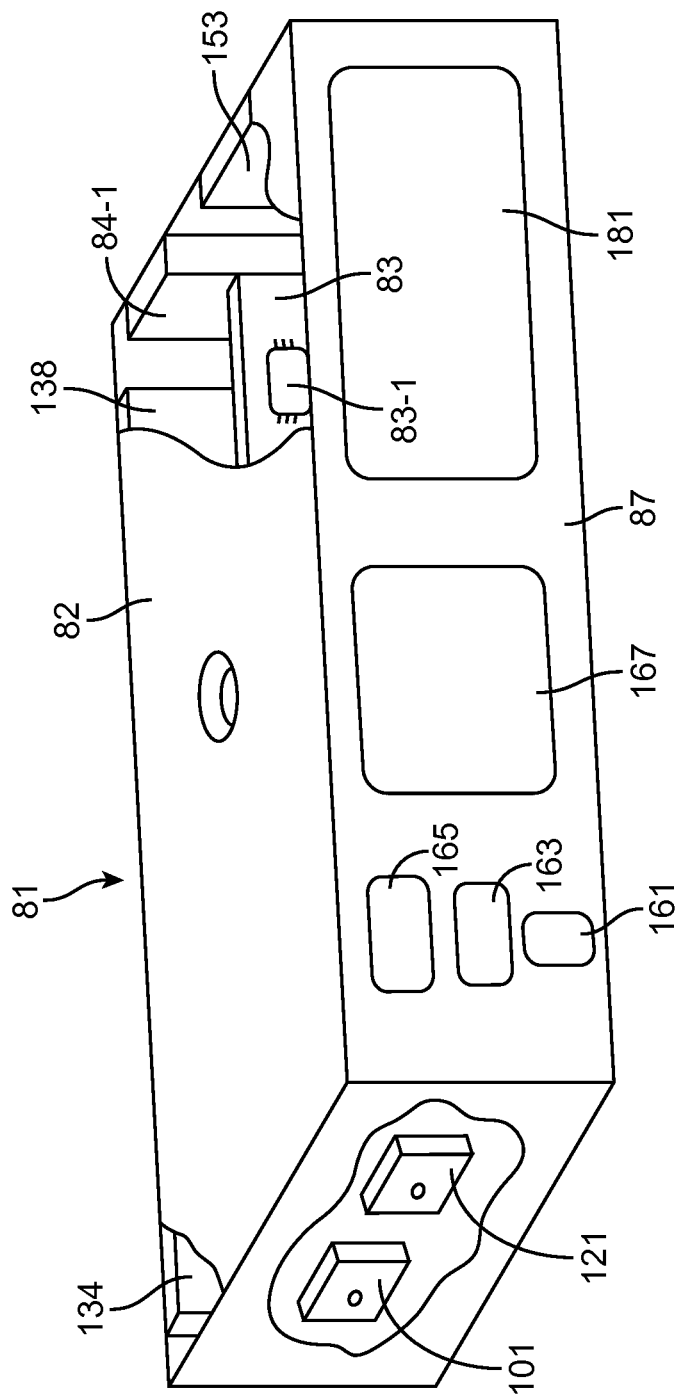
FIG. 7(a) is an enlarged fragmentary view, broken away in part, of the control unit of the fluid management and monitoring system shown in FIG. 1.
Figure 7B:
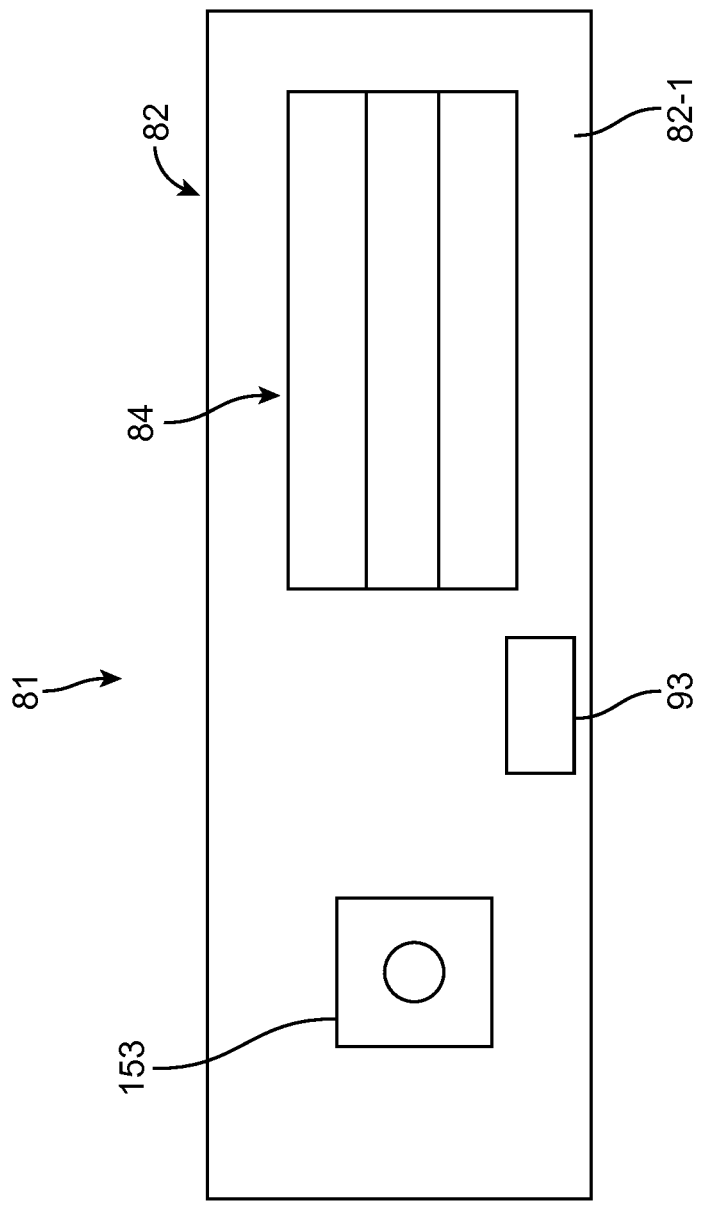
FIG. 7(b) is a side view of the control unit shown in FIG. 7(a)

The fluid management and monitoring system may further comprise a control unit 81 mounted on top of support beams 55-1 and 55-2. Control unit 81, which is also shown in FIGS. 7(a) and 7(b), may comprise a generally rectangular housing 82. A main circuit board 83 having a microprocessor 83-1 may be mounted within housing 82. A peristaltic fluid pump 84 may be mounted on an exterior side face 82-1 of housing 82. Pump 84 may be electrically connected by means not shown to a pump circuit board 84-1 positioned within housing 82, board 84-1 being electrically connected to main circuit board 83 by means not shown. Control unit 81 may also comprise an interactive control panel 87 positioned along a front face 82-2 of housing 82, panel 87 being coupled to main circuit board 83 by means not shown.

The fluid management and monitoring system may further comprise a Y-tubing set 89 having a first inlet end 89-1 fluidly coupled to bag 73 and a second inlet end 89-2 fluidly coupled to bag 74. A removable clamp 90 may be attached to Y-tubing set 89 near first inlet end 89-1 or near second inlet end 89-2 so that only one of bags 73 and 74 drains at a time. The outlet end 89-3 of Y-tubing set 89 may be fed into fluid pump 84.

The fluid management and monitoring system may further comprise a fluid tubing 91, one end of fluid tubing 91 being fluidly connected at pump 84 to outlet end 89-3 of Y-tubing set 89, the opposite end of tubing 91 being fluidly connected to fluid input port 15 of hysteroscope 13.

The fluid management and monitoring system may further comprise a fluid pressure sensor 93 (shown in FIG. 7(b)) as part of control unit 81, sensor 93 being mounted on side face 82-1 of housing 82 and being electrically connected to main circuit board 83 by means not shown. Sensor 93 may be used to gauge, through back pressure, the fluid pressure in the uterus (or other body cavity) where fluid has been delivered via channel 23-1 of hysteroscope 13. In this manner, if sensor 93 senses that the fluid pressure is below a predetermined threshold, control unit 81 may cause pump 84 to be actuated to increase the flow of fluid to the uterus. On the other hand, if sensor 93 senses that the fluid pressure has reached a predetermined threshold, control unit 81 may cause pump 84 to be deactivated.

The fluid management and monitoring system may further comprise a pair of independently controllable vacuum systems. A first such vacuum system may comprise a vacuum source 101 positioned within housing 82 (see FIG. 7(a)). Vacuum source 101, which may be conventional in construction and which may be connected to main circuit board 83 by means not shown, may be fluidly coupled through a length of tubing 103 to a first collection container 105 seated on gravimetric scale 57. First collection container 105 may be fluidly coupled through a length of tubing 107 to a second collection container 109 seated on gravimetric scale 57. Second collection container 109, in turn, may be fluidly coupled through a length of tubing 111 to inner tubular member 47 of tissue removal device 41. In this manner, as tissue removal device 41 is operated, vacuum pressure from source 101 is applied to the patient through resection window 49 of device 41. As tissue is cut from the patient using device 41, such tissue is conveyed from the patient through device 41 using the vacuum pressure and is collected in collection containers 109 and/or 105. It should be noted that, at the same time that the resected tissue is withdrawn from the patient in the above manner, some of the distending fluid from inside the patient is also withdrawn from the patient through device 41 and is collected in collection containers 109 and/or 105. This may cause a temporary net loss in the volume of distending fluid that is present within the patient until pump 84 has pumped a sufficient volume of replacement distending fluid into the patient. This issue is addressed further below.

The second of the two independently controllable vacuum systems may comprise a vacuum source 121 positioned within housing 82 (see FIG. 7(a)). Vacuum source 121, which may be conventional in construction and which may be electrically connected to main circuit board 83 by means not shown, may be fluidly coupled through a length of tubing 123 to a third collection container 125 seated on gravimetric scale 57. Third collection container 125, in turn, may be fluidly coupled through a length of tubing 127 to a collection bag or drape 129 positioned relative to the patient to collect distending fluid that may leak from the patient during the procedure. In this manner, vacuum pressure from source 121 may be continuously applied to drape 129. Therefore, as fluid from the patient is collected in drape 129, such fluid may be conducted from drape 129 to collection container 125.

As can be appreciated, because vacuum source 101 and vacuum source 121 are independently controllable, vacuum source 101 may be operated at a comparatively high pressure, and vacuum source 121 may be operated at a comparatively low pressure. For example, vacuum source 101 may be fixed or adjustable for pressures in the range of approximately 200-500 mmHg, which may be optimal for operation of device 41. By contrast, vacuum source 121 may be fixed or adjustable for operation at pressures of approximately 50-150 mmHg, which may be adequate to drain drape 129, without causing drape 129 to collapse onto itself due to excessive pressure or to make an undesirable whistling sound as may occur when high vacuum pressure is applied to an empty drape.

If desired, vacuum source 101 and vacuum source 121 may be replaced with a single vacuum source having two independent outlets of different suction strength.

As noted above, the fluid management and monitoring system of the embodiments may include a gravimetric scale 57 on which containers 105, 109, and 125, as well as fluid stand 61, may be seated. Scale 57 may be electrically connected to a circuit board 134 in housing 82 via a cable 135, circuit board 134 in turn being electrically connected to main circuit board 83 by means not shown. Scale 57 may be used to continuously determine the combined weight of the distending fluid that has been collected from the patient and the unused distending fluid that remains in fluid bags 73, 74 and 76. This combined weight may be used by microprocessor 83-1 to determine the current fluid deficit of the patient by subtracting the combined weight of the fluid from the starting weight of the fluid in bags 73, 74 and 76. This weight may then be converted by microprocessor 83-1 into a volume, i.e., the current fluid deficit, using the known density of the distending fluid. The current fluid deficit may then be displayed on control panel 87.

In addition, the current fluid deficit may also be displayed on a deficit display 137 positioned proximate to monitor 39, such as by being fixedly or removably mounted on monitor 39. As can be appreciated, one benefit to positioning display 137 proximate to monitor 39 is that the doctor can view display 137, and therefore, be kept abreast of the current fluid deficit, without turning away from monitor 39, on which the procedure is shown. The current fluid deficit data may be transmitted from control unit 81 to display 137 either wirelessly, e.g., using Bluetooth or WIDI (wireless direct interface), or through a wire. In the illustrated embodiment, the current fluid deficit data is transmitted wirelessly from control unit 85 to display 137 using a transmitter 138 (see FIG. 7(a)) positioned within housing 82 and coupled to main circuit board 83 by means not shown and a receiver 139 coupled to and mounted on display 137.

System 11 may further comprise a mechanism for the coordinated actuation of tissue removal device 41 and fluid pump 84. As noted above, an unintended consequence of using device 41 is that some of the distending fluid used to distend the patient's uterus is withdrawn from the patient through device 41 during operation of device 41. Although system 11 may comprise a pressure sensor 93 that may be used to sense when the fluid pressure drops below a preset value and when pump 84 should be actuated to deliver replacement distending fluid, the drop in pressure may be precipitous, particularly if a high suction pressure is applied. A steep drop in uterine fluid pressure may result in the rupturing of uterine blood vessels, causing undesired bleeding, and may also result in the return of the uterus to its original flaccid state. Moreover, depending on the extent and speed of the drop in uterine fluid pressure, there may be a significant lapse of time before the uterine fluid pressure can be restored to a desired level. Such lapses in time are clearly undesirable as they interrupt the resection procedure, as well as lengthen the overall time for the procedure and increase the risk of intravasation.

Consequently, system 11 may comprise a shared switch used to actuate both the operation of tissue removal device 41 and the operation of fluid pump 84. In this manner, fluid pump 84 may begin to pump replacement distending fluid earlier than it would otherwise if actuated only after a drop in fluid pressure has been detected by sensor 93. This arrangement may comprise a pneumatic foot switch 141. Switch 141 may be fluidly coupled to a first tube 142, which, in turn, may be fluidly coupled via a tee 143 to a second tube 145 and to a third tube 147. Second tube 145 may be fluidly coupled to a pneumatic switch 149 on a control unit 151 that is electrically coupled to device 41 via a cable 152. Third tube 147 may be fluidly coupled to a pneumatic switch 153 on control unit 81 that is electrically coupled to main circuit board 83 by means not shown. According to the above arrangement, depression of foot switch 141 causes pneumatic switches 149 and 153 to be closed simultaneously. The simultaneous closing of switches 149 and 153 may cause the simultaneous actuation of device 41 and pump 84.

Figure 8:
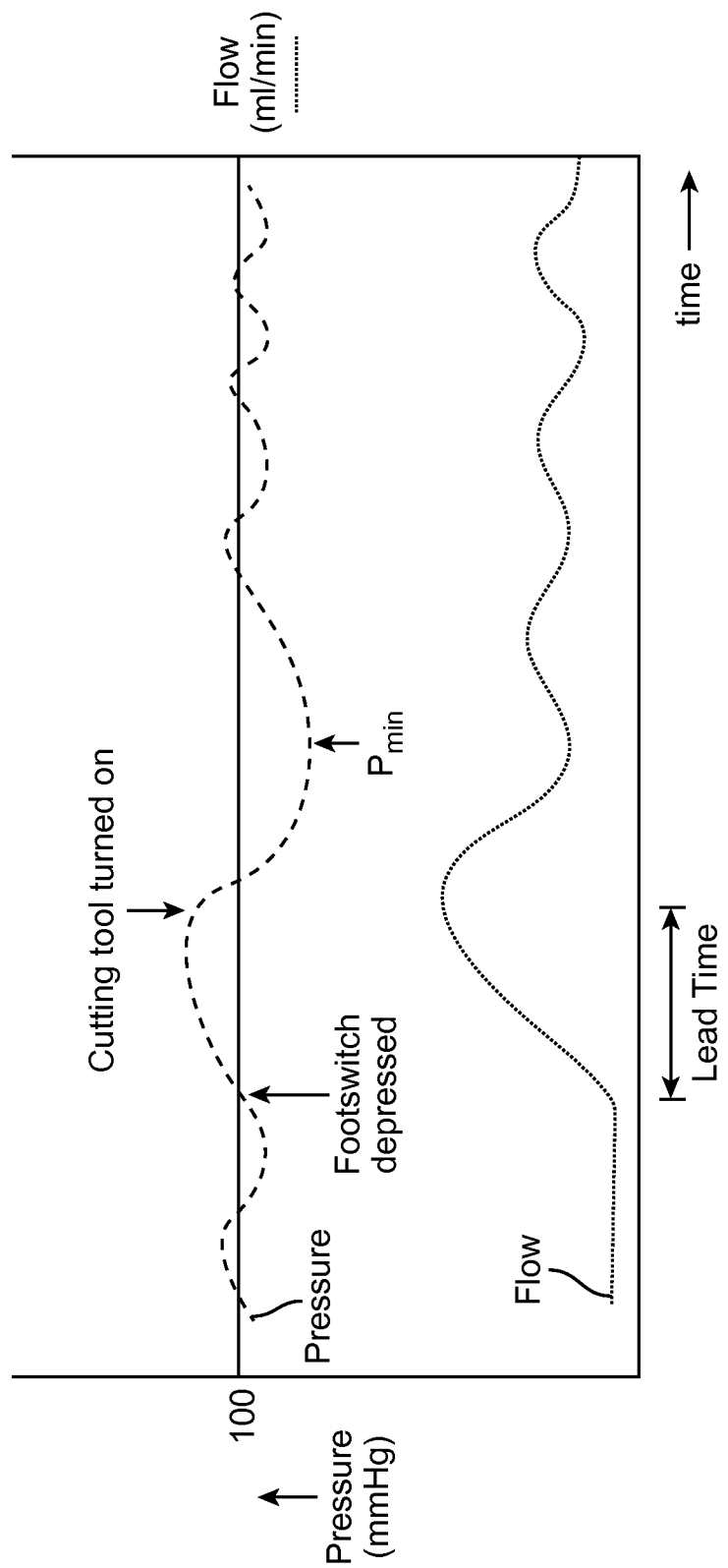
FIG. 8 is a qualitative graphic representation of uterine fluid pressure over time for an exemplary system in which a common switch is used for coordinated actuation of a tissue removal device and a fluid pump, with the actuation of the tissue removal device being delayed relative to actuation of the fluid pump.

Alternatively, control unit 151 may include a delay circuit to delay actuation of device 41 relative to actuation of pump 84 by a desired time interval to minimize the drop in uterine fluid pressure from a desired level (e.g., 100 mmHg). FIG. 8 qualitatively depicts the uterine fluid pressure over time where the actuation of device 41 is delayed relative to the actuation of pump 84. As can be seen, because pump 84 may start before device 41 begins to operate, there may be a transient period of time during which the fluid pressure in the patient may exceed the threshold (shown as 100 mmHg) at which sensor 93 shuts off pump 84. Control unit 81 may be configured so as not to shut pump 84 off during this transient period or may be configured so as to shut pump 84 off during this period only if the fluid pressure exceeds an elevated threshold (e.g., 120 mmHg) that is in excess of the normal threshold (e.g., 100 mmHg).

As can be appreciated, although the above arrangement for sending simultaneous signals to switches 149 and 153 is pneumatically-based, one could alternatively use an electrical arrangement (although a pneumatic arrangement may have an advantage over an electrical arrangement insofar as the pneumatic arrangement does not need to guard against electrical shorting caused by contact of the arrangement with the distending fluid or with other liquids). Also, instead of using foot switch 141 to simultaneously send signals to switches 149 and 153, one could use foot switch 141 to send a signal to switch 149 and could then use a cable to send a signal from control unit 151 to control unit 81 or could use foot switch 141 to send a signal to switch 153 and could then use a cable to send a signal from control unit 81 to control unit 151.

Figure 9:
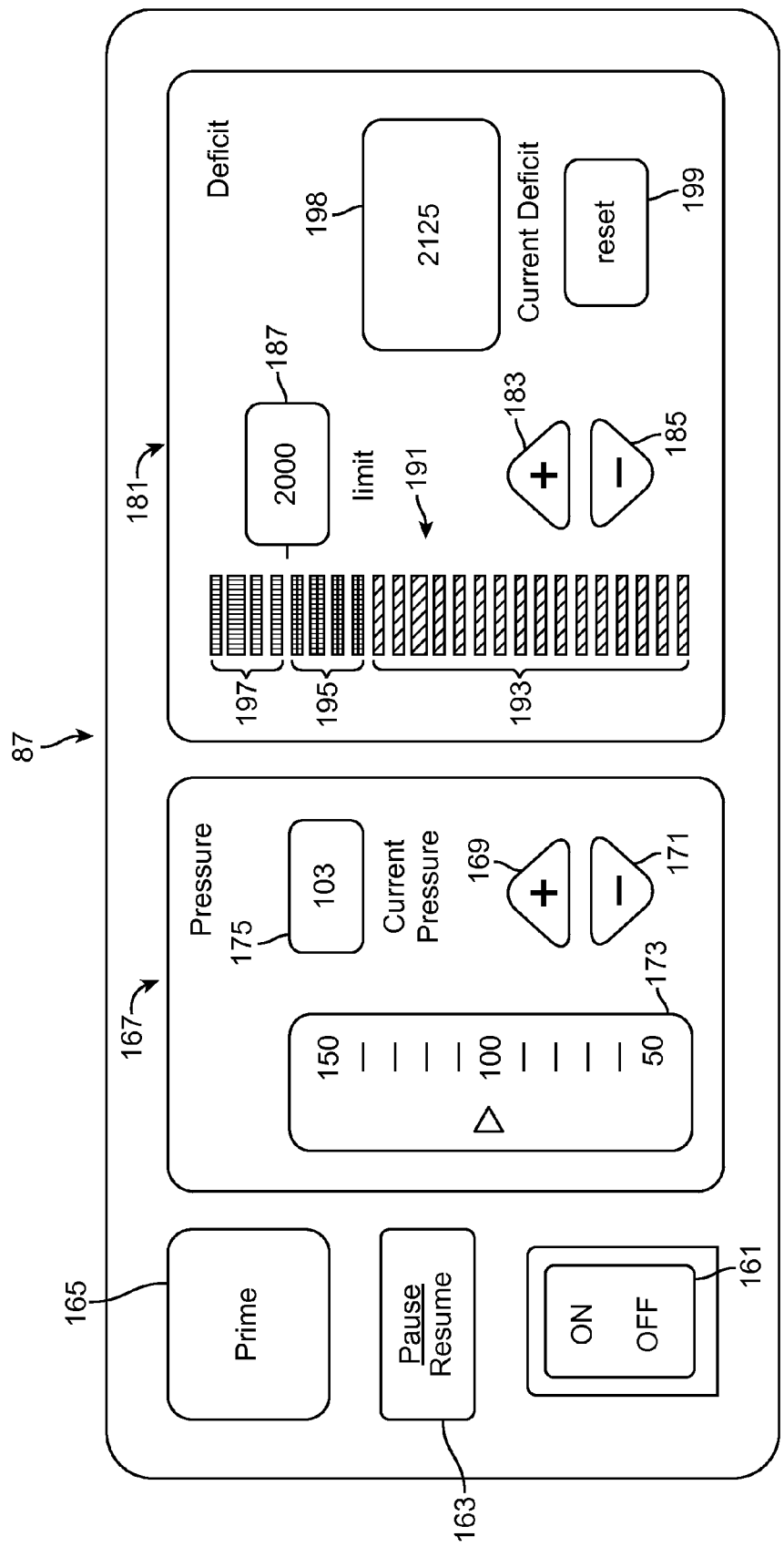
FIG. 9 is an enlarged front view of the interactive control panel for the control unit of the fluid management and monitoring system shown in FIG. 1.

Referring to FIG. 9, there is shown an enlarged view of interactive control panel 87. As can be seen, control panel 87 may comprise an on/off button 161 for use in turning control unit 81 off or on and may also comprise a pause/resume button 163 for use in temporarily pausing the operation of control unit 81. In addition, panel 87 may also comprise a prime button 165 for use in causing pump 84 to be primed.

Control panel 87 may further comprise a pressure display panel 167. Pressure display panel 167 may comprise an "up" button 169 and a "down" button 171 for use in setting a desired fluid pressure threshold, as well as an analog display 173 for displaying the set fluid pressure threshold and a digital readout 175 for displaying the fluid pressure currently being detected.

Control panel 87 may further comprise a fluid deficit display panel 181. Deficit display panel 181 may comprise an "up" button 183 and a "down" button 185 for use in setting a desired fluid deficit limit, which limit may range from about 800-2500 cc. Deficit display panel 181 may also comprise a digital readout 187 for displaying the set fluid deficit limit. Panel 181 may also comprise a multicolor digital bar graph meter 191. Meter 191 may comprise a plurality of LEDs or other illuminable bars arranged in a vertical scale for graphically representing the current fluid deficit as a fraction of the limit displayed in readout 187. A first portion 193 of digital bar graph meter 191, which may start at the bottom of meter 191 and which may extend proportionately upwardly to about "x" percentage (e.g., 60%) of the fluid deficit limit, may light in a first color, such as green, to depict a current fluid deficit in a "comfortable zone." A second portion 195 of digital bar graph meter 191, which may start where portion 193 ends and which may extend proportionately upwardly to about "x+y" percentage (e.g., 90%) of the fluid deficit limit, may light in a second color, such as yellow, to depict a current fluid deficit in a "caution zone." A third portion 197 of digital bar graph meter 191, which may start where portion 195 ends and which may extend to the top of meter 191, may light in a third color, such as red, to depict a current fluid deficit in a "danger zone." Display panel 181 may further comprise a digital readout 198 for displaying the current fluid deficit being detected. The read-out of readout 198 may be shown in a color that matches the color of the current fluid deficit as depicted by multicolor digital bar graph meter 191. Display panel 181 may further comprise a reset button 199 for use in resetting the current fluid deficit.

It will be appreciated that system 11 may be used in the fashion described and discussed above. It should be noted, however, that, prior to insertion of device 41 through hysteroscope 13 and into the patient's uterus, a sufficient quantity of distending fluid should be delivered to the patient's uterus through hysteroscope 13 to adequately expand the uterus and to rinse the uterus of blood and other unwanted matter. During this expansion/rinsing procedure, a conventional outflow channel (not shown) may be inserted into channel 23-1 of hysteroscope 13 and attached to collection container 109.

Figure 10:
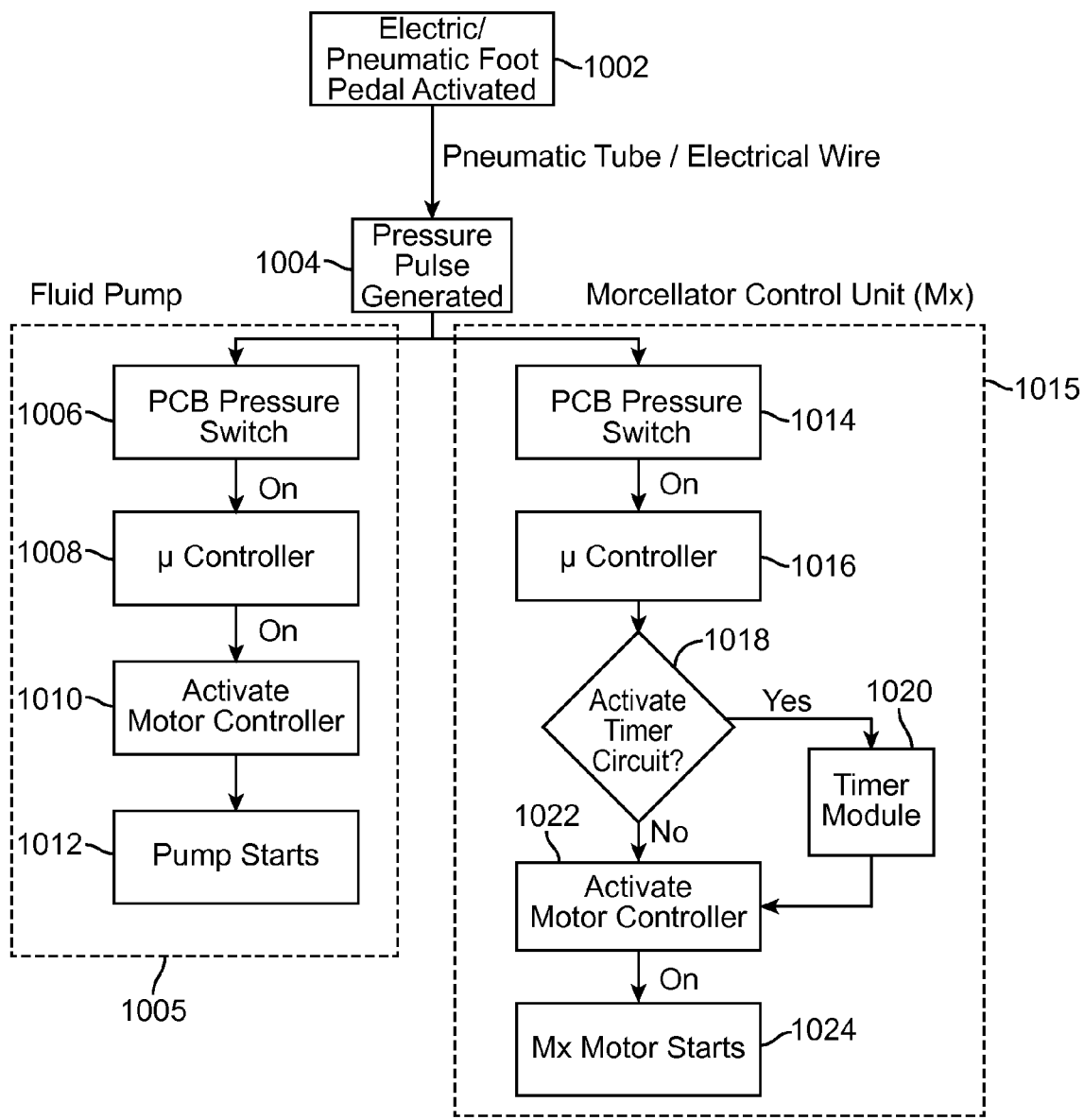
FIG. 10 is a system component diagram of an embodiment of the hysteroscopic tissue removal system having a pneumatic configuration.

With reference to FIG. 10 there is illustrated a system component diagram of an embodiment of the hysteroscopic tissue removal system having a pneumatic configuration. As depicted, an electric or pneumatic foot pedal can be activated by a surgeon at block 1002. The pneumatic foot pedal is coupled to a pneumatic tube that is coupled to a fluid pump 1005 and a morcellator control unit 1015. When the pneumatic foot pedal is activated at block 1002, a pressure pulse is generated at 1004 and the pressure pulse is transmitted to fluid pump 1005 and morcellator control unit 1015. When the pressure pulse is received at fluid pump 1005 a printed circuit board (PCB) pressure switch at block 1006 is activated. It will be appreciated that other like devices can be used in lieu of a PCB pressure switch. In activating the PCB pressure switch at block 1006, a microcontroller is activated at block 1008, which in turn activates the motor controller at block 1010. The motor controller at block 1010 proceeds to activate the pump at block 1012 to start pumping inflow fluid into the surgical site through the introducer device 7.

When the pressure pulse is transmitted to the morcellator control unit 1015, the pressure pulse is received by PCB pressure switch 1014 which activates the microcontroller 1016. At decision point 1018, the microcontroller determines whether to activate a timer circuit. If the timer circuit is activated, then timer module 1020 is activated and the motor controller is activated at block 1022 after a period of time has passed. If the timer circuit is not activated at decision point 1018, then the motor controller is activated at block 1022 without any delay. The activated motor controller then activates the morcellator motor at block 1024. The foregoing process has been described in the context of using a pressure pulse generated from a pneumatic foot pedal, however, a similar process can be used for an electrical signal generated by an electric foot pedal. In the context of an electrical signal, the process would likely not include a PCB pressure switch but rather the electrical signal would be transmitted directly to the microcontrollers 1008, 1016.

Figure 11:
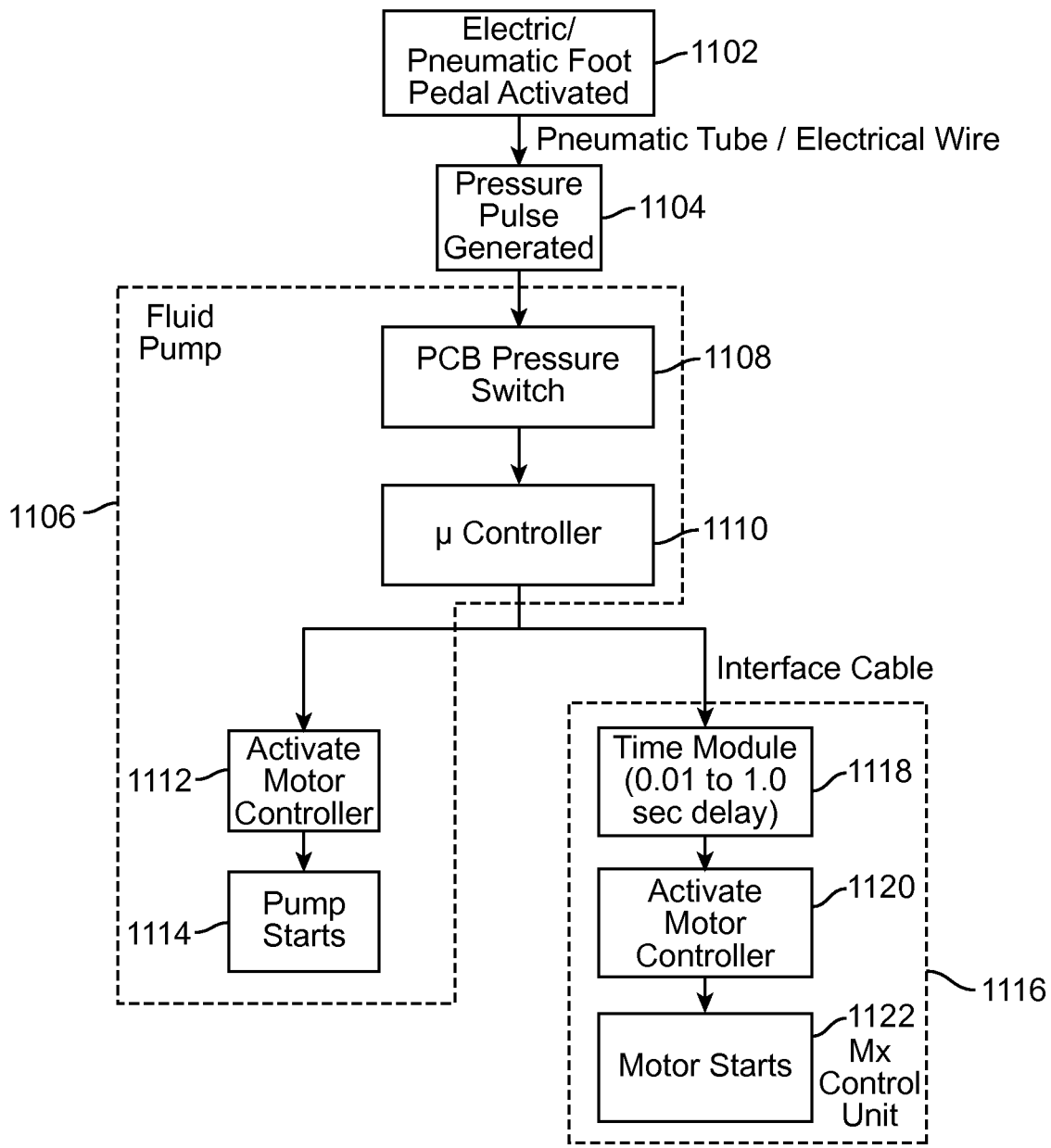
FIG. 11 is a system component diagram of an embodiment of the hysteroscopic tissue removal system having an electronic configuration.

Referring to FIG. 11, there is illustrated a system component diagram of an embodiment of the hysteroscopic tissue removal system having an electronic configuration. In an embodiment, a user can activate an electric or pneumatic foot pedal at block 1102. The electric or pneumatic foot pedal can be coupled to a pneumatic tube or electrical wire. In the context of a pneumatic tube, the pneumatic tube can be coupled to a PCB pressure switch 1108. After the pneumatic foot pedal is activated by the user, a pressure pulse is generated at block 1104 and is transmitted to the PCB pressure switch 1108. The PCB pressure switch 1108 activates the microcontroller 1110. The microcontroller can be housed within fluid pumped system 1106. The microcontroller 1110 can be configured to send an electrical signal to activate the motor controller at block 1112.

The activated motor controller 1112 can then start the inflow pump at block 1114 to start pumping inflow fluid into the surgical site through the introducer device 7. The microcontroller 1110 can also be configured to send an electrical signal to the timer module 1118 within morcellator control unit 1116. The timer control module 1118 can be configured to activate the motor controller at block 1120 after a period of time has passed. The activated motor controller 1120 can then start the motor at block 1122 for driving the morcellator configured to cut tissue at the surgical site. The foregoing process has been described with respect to a pressure pulse generated by a pneumatic foot pedal, however, a similar process can be utilized for an electrical signal generated by an electric foot pedal. In the context of an electrical signal generated by an electric foot pedal, the electrical signal is transmitted directly to the microcontroller 1110, and no PCB pressure switch is necessary.

Figure 12:
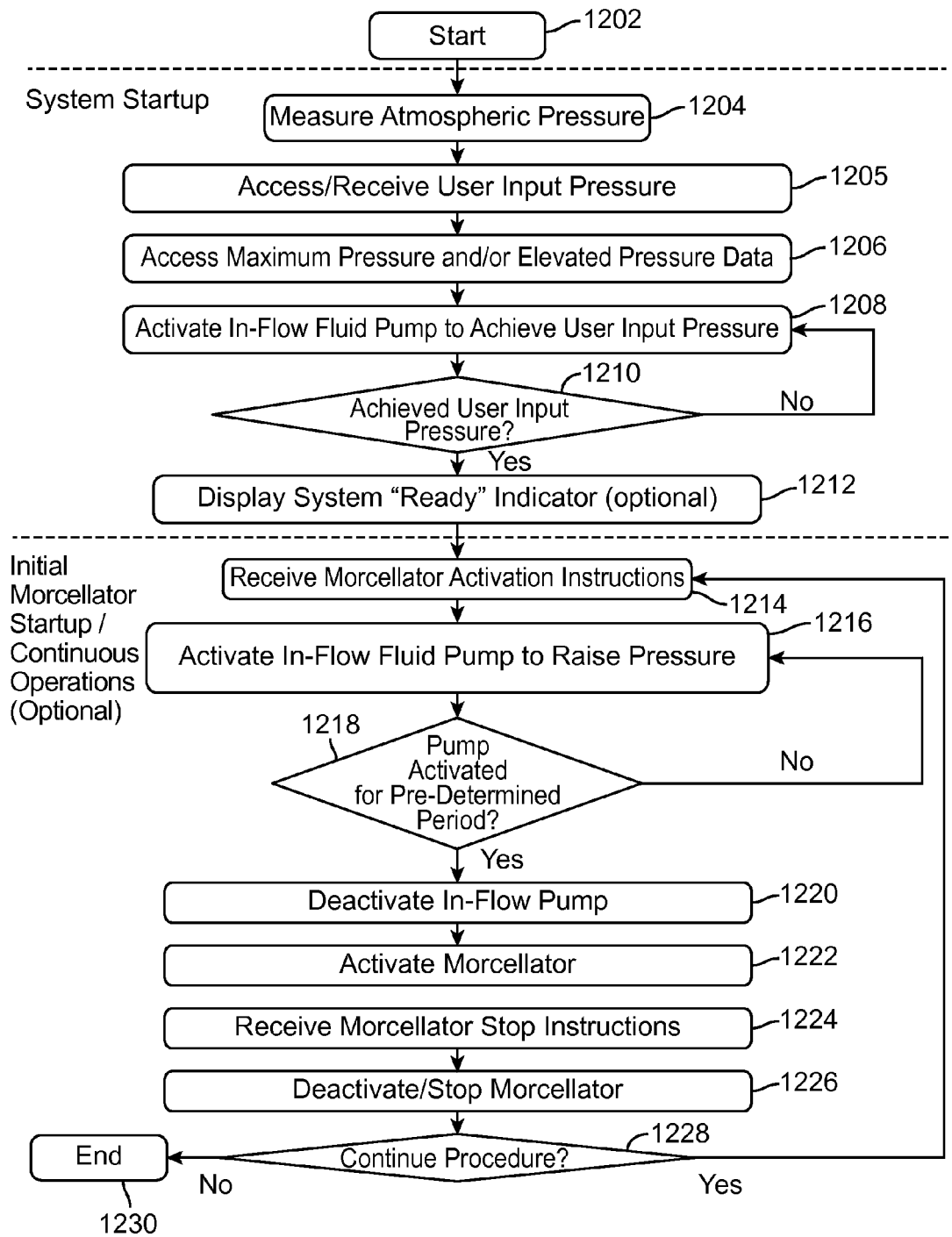
FIG. 12 is a flow chart depicting an embodiment of a process for activating and/or using the hysteroscopic tissue removal system.

With respect to FIG. 12, there is illustrated a flow chart depicting an embodiment of a process for activating and/or using the hysteroscopic tissue removal system. The process can start at block 1202, wherein the system can be configured to measure the atmospheric pressure at 1204. At block 1205, the system can access and/or receive user input pressure data. For example, the surgeon can enter the desired fluid pressure level at the surgical site (for example, 80 mm Hg). At block 1206, the system can access the maximum pressure and/or elevated pressure data. As discussed above, the system can be configured to utilize the maximum pressure and/or elevated pressure data to determine the elevated pressure threshold level to be achieved before activating the morcellator.

At block 1208, the system activates the inflow fluid pump to start pumping fluid into the surgical site to achieve the desired fluid pressure that was input by the user. At block 1210, the system determines whether the desired fluid pressure at the surgical site has been achieved. If the desired fluid pressure has not been achieved then the system continues to pump inflow fluid into the surgical site at block 1208. If the desired fluid pressure level has been achieved, then the system proceeds to block 1212 and optionally displays the "ready" indicator to the user. At block 1212, the system start up portion of the process has been completed. At this stage, the system may be used by the surgeon to remove tissue from a surgical site using a morcellator. At block 1214, the system receives a morcellator activation instruction from the user.

At block 1216, the system can be configured to activate the inflow fluid pump to raise the pressure level at the surgical site. At decision block 1218, the system can be configured to determine whether the inflow fluid pump has been pumping fluid into the surgical site for a predetermined period of time. If the system has not been pumping inflow fluid into the surgical site for the predetermined period, then the system continues pumping inflow fluid into the surgical site at block 1216. If the system has pumped fluid into the surgical site for the predetermined period, then the system can deactivate the inflow fluid pump at block 1220.

At block 1222, the system can activate the morcellator to allow the surgeon to begin cutting tissue at the surgical site. At block 1224, the system can receive a morcellator stop instruction from the user. At block 1226, the system can deactivate or stop the morcellator based upon receiving the morcellator stop instructions from the user. At decision block 1228, the system determines whether the user wishes to continue with the procedure or end the procedure. If the user wishes to proceed with this procedure, the system proceeds to block 1214 and waits to receive morcellator activation instructions from the user. If the system determines that the user wishes to end the procedure, the system can proceed to block 1230 to end the process.

Figure 13:
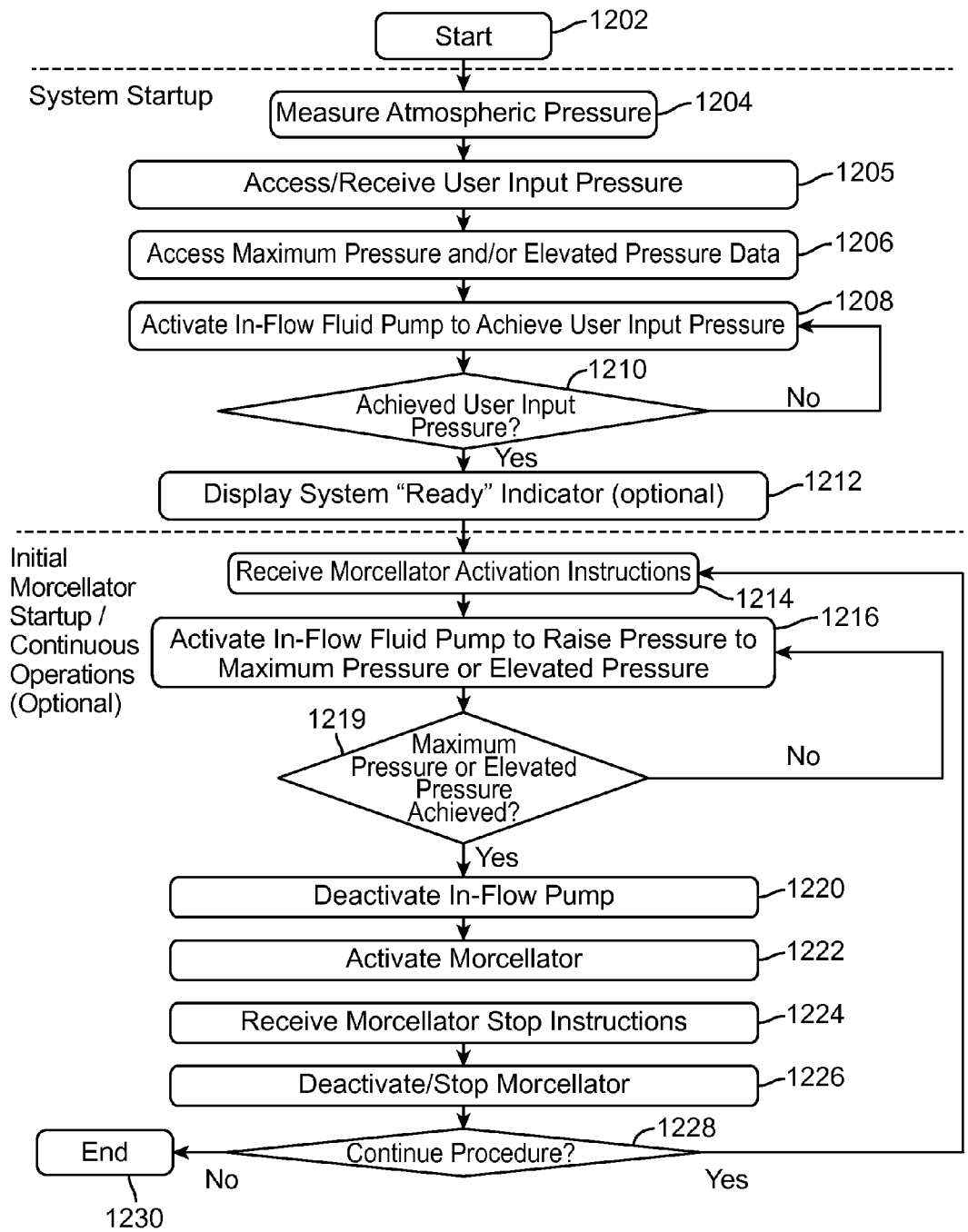
FIG. 13 is a flow chart depicting an embodiment of a process for activating and/or using the hysteroscopic tissue removal system.

Referring to FIG. 13, there is illustrated a flow chart depicting an embodiment of a process for activating and/or using the hysteroscopic tissue removal system. The process can start at block 1202, where the system can measure the atmospheric pressure at block 1204. The system can access and/or receive user input pressure at block 1205 as described above. At block 1206, the system can access maximum pressure and/or elevated pressure data. The system at block 1208 can activate the inflow fluid pump to achieve the user's desired fluid pressure level at the surgical site. At decision point 1210 the system determines whether the desired fluid pressure level has been achieved at the surgical site. If the desired fluid pressure level at the surgical site has not been achieved, the system continues to pump fluid into the surgical site at block 1208. If the desired fluid level pressure has been achieved, then the system at block 1212 optionally displays the system "ready" indicator. At this point, the system start up process is complete, and the system enters the morcellator start up or continuous operations stage.

At block 1214, the system can receive morcellator activation instructions from the user. At block 1216, the system activates the inflow fluid pump to raise the fluid level pressure at the surgical site. The system can be configured to increase the fluid pressure level at the surgical site to reach the maximum pressure or to reach the elevated pressure based on the maximum pressure and/or elevated pressure data previously accessed by the system. At decision block 1219, the system determines whether the maximum pressure or the elevated pressure has been achieved at the surgical site. If the maximum pressure or the elevated pressure has not been achieved at the surgical site, then the system continues to pump inflow fluid into the surgical site at block 1216. If the system determines that the maximum pressure or the elevated pressure has been achieved at the surgical site, then the system deactivates the inflow fluid pump at block 1220.

The system at block 1222 can activate the morcellator to allow the surgeon proceed to cut tissue at the surgical site. At block 1224, the system can receive morcellator stop instructions from the user. The system at block 1226 can deactivate or stop the morcellator. At decision block 1228, the system determines whether the surgeon wishes to proceed or continue with the procedure. If the system determines that the user wishes to proceed with the surgical procedure, then the system proceeds to block 1214 and awaits to receive morcellator activation instructions from the user. If the system determines that the surgeon does not wish to continue with the procedure, the system moves to block 1230 to end the process.

Figure 14:
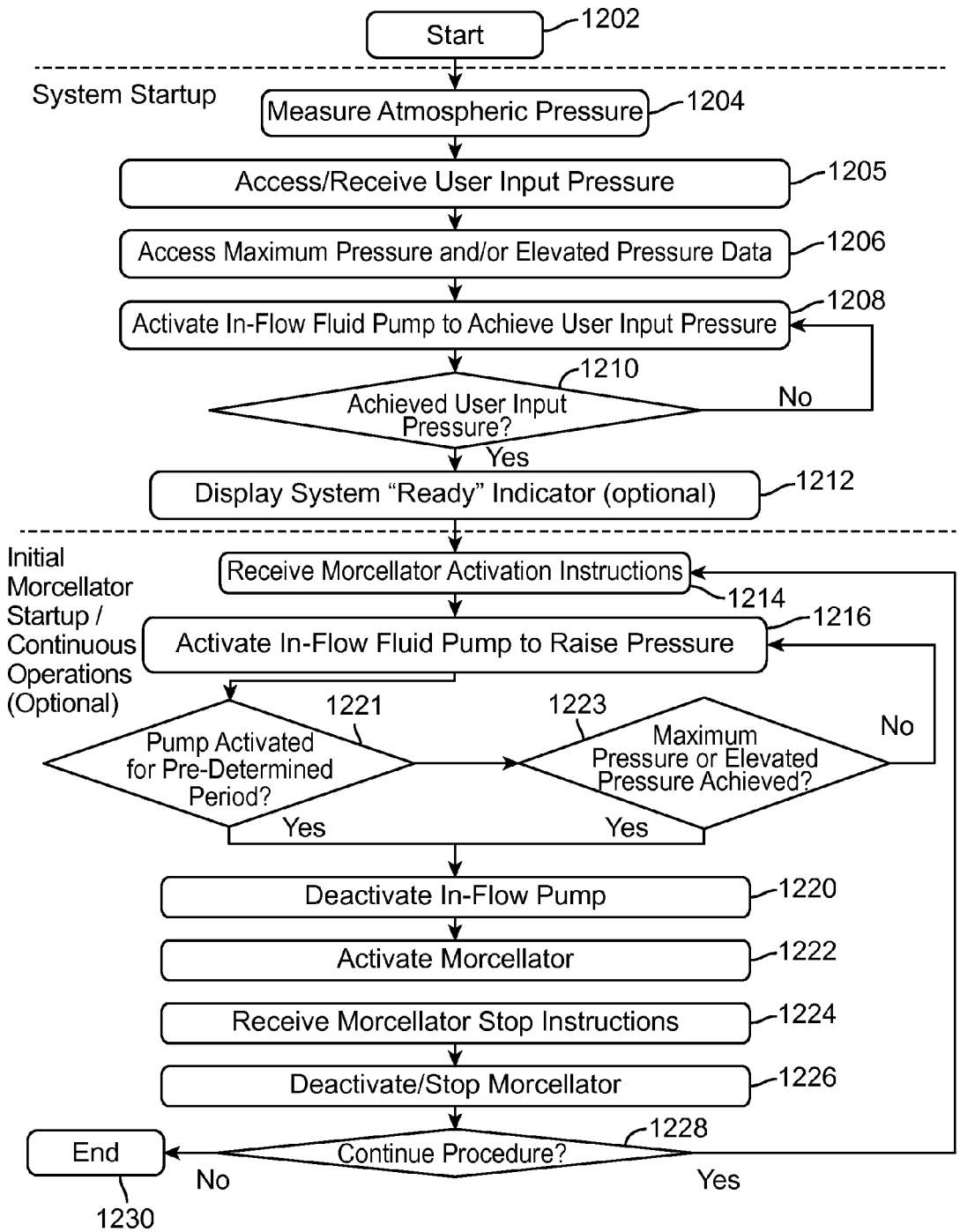
FIG. 14 is a flow chart depicting an embodiment of a process for activating and/or using the hysteroscopic tissue removal system.

Referring to FIG. 14, there is illustrated a flow chart depicting an embodiment of a process for activating and/or using the hysteroscopic tissue removal system. In an embodiment this process can start at block 1202 and proceed to block 1204 where the system measures the atmospheric pressure. In an embodiment, the system can be configured to determine pressure at the distal end of the introducer or scope outlet based in part on the atmospheric pressure. The pressure at the distal end of the introducer or hysteroscope outlet is equivalent or substantially the same as the fluid pressure level at the surgical site.

In one embodiment, the system measures the atmospheric pressure at the pump head 9(*b*) before start up and/or before anything is connected to the pump head. When the tubing and introducer/hysteroscope are connected to the pump head, the pump can be configured to operate through a calibration routine that measures the pressure at the pump head at various flow rates. In one embodiment, the system can be configured to calculate the difference between the original atmospheric pressure reading and the pressure reading when pushing fluid through the tubing and introducer/hysteroscope into the atmospheric pressure. From this pressure differential, or flow impedance, the system can determine the pressure at the distal end of the introducer/hysteroscope outlet and at the surgical site. Alternatively, the system can be configured with a pressure sensor at the distal end of the introducer or hysteroscope to determine the fluid pressure at the surgical site.

At block 1205, the system can access and/or receive the user's desired pressure level to be achieved at the surgical site. The system can access maximum pressure and/or elevated pressure data at block 1206 as described above. At block 1208 the system can activate the inflow fluid pump to achieve the user's desired fluid pressure level at the surgical site.

At decision block 1210, the system determines whether the user's desired fluid pressure level has been achieved at the surgical site. If the user's desired fluid pressure level has not been achieved at the surgical site, then the system continues to pump inflow fluid into the surgical site at block 1208. If the system determines that the fluid pressure level at the surgical site has achieved the user's desired fluid level pressure, then the system at block 1212 can optionally display the "ready" indicator to the user. At this stage, the system start up process has been completed and the process can now enter the initial morcellator start up or continuous operations stage. At block 1214, the system can receive morcellator activation instructions from the user.

At block 1216, the system activates the inflow fluid pump to raise the fluid pressure level at the surgical site. At decision block 1221, the system determines whether the inflow fluid pump has been activated for a predetermined period of time. If the system determines that the inflow fluid pump has been activated for a predetermined period, then the system deactivates the inflow fluid pump at block 1220. If the system determines that the inflow fluid pump has not been activated for the predetermined period, then the system proceeds to decision block 1223 to determine whether the maximum pressure or the elevated pressure level has been achieved at the surgical site. If the system determines that the pressure level at the surgical site has not achieved the maximum pressure level or the elevated pressure level, then the system continues to pump inflow fluid into the surgical site at block 1216. If the system determines that the maximum pressure or the elevated pressure level has been achieved at the surgical site, then the system deactivates the inflow fluid pump at block 1220.

At block 1222, the system activates the morcellator to allow the surgeon to cut tissue at the surgical site. At block 1224, the system can receive morcellator stop instructions from the user. The system deactivates or stops the motor at block 1226. At decision block 1228, the system determines whether the user wishes to continue with the surgical procedure. If the system determines that the user wishes to proceed with the surgical procedure, then at block 1214 the system waits to receive morcellator activation instructions.

If the system determines that the user wishes to end the surgical procedure, then the system moves to block 1230 to end the process.

Figure 15:
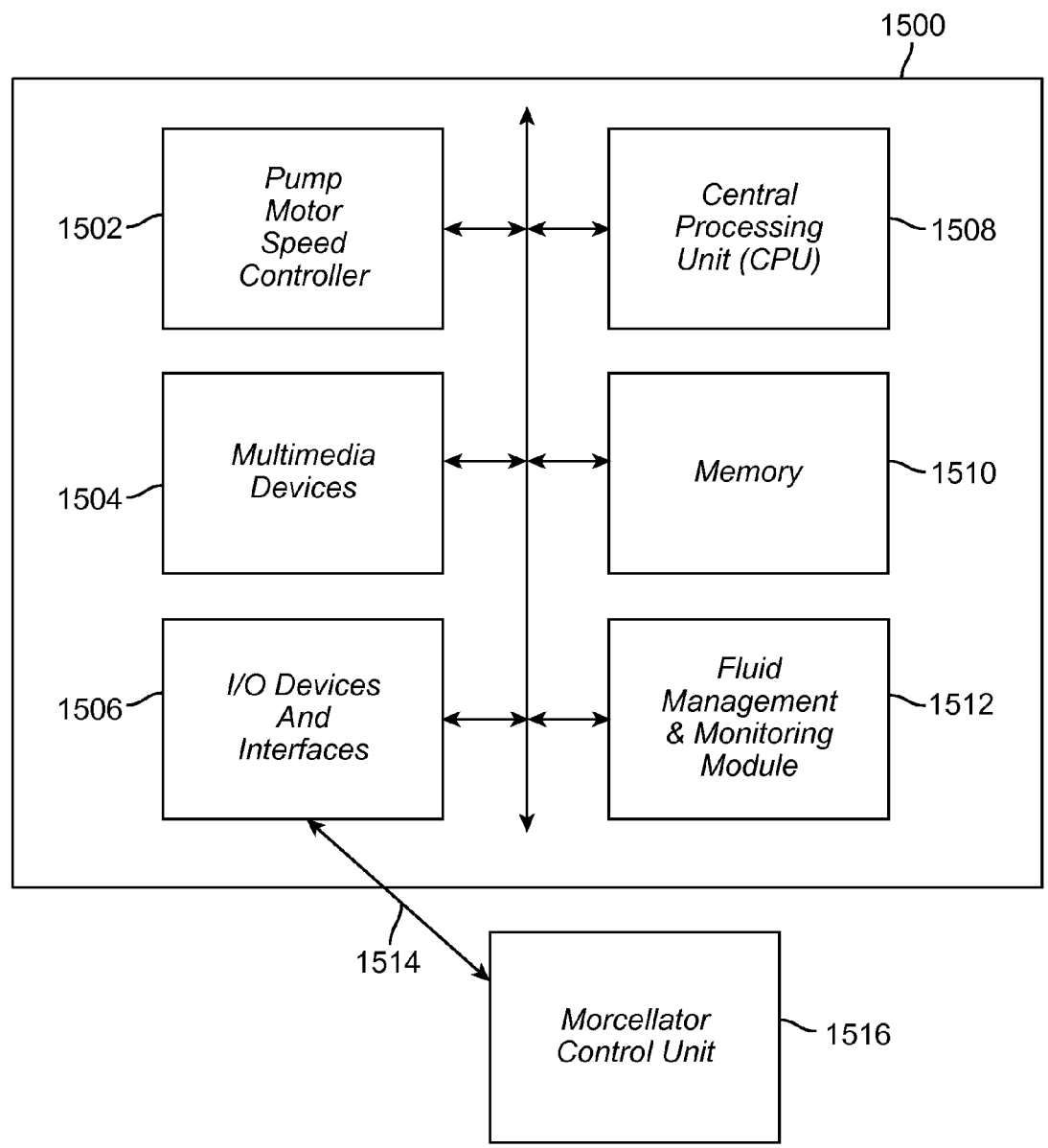
FIG. 15 is a block diagram depicting an embodiment of a computer hardware system configured to run software for implementing one or more embodiments of the hysteroscopic tissue removal system.

In some embodiments, the systems, processes, and methods described above are implemented using a computing system, such as the one illustrated in FIG. 15. The computer system 1500 is in communication with one or more morcellator control units 1516. While FIG. 15 illustrates an embodiment of a computing system 1500, it is recognized that the functionality provided for in the components and modules of computer system 1500 may be combined into fewer components and modules, or further separated into additional components and modules.

The computer system 1500 includes a Fluid Management & Monitoring Module 1512 that carries out the functions, methods, acts, and/or processes described herein. The Fluid Management & Monitoring Module 1512 is executed on the computer system 1500 by a central processing unit 1508 discussed further below. In general, the word "module," as used herein, refers to logic embodied in hardware or firmware or to a collection of software instructions, having entry and exit points. Modules are written in a program language, such as JAVA, C or C++, or the like. Software modules may be compiled or linked into an executable program, installed in a dynamic link library, or may be written in an interpreted language such as BASIC letters, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1500 includes one or more processing units (CPU) 1508, which may include a microprocessor. The computer system 1500 further includes a memory 1510, such as random access memory (RAM) for temporary storage of information, a read only memory (ROM) for permanent storage of information. The computer system 1500 can comprise a mass storage device, such as a hard drive, diskette, or optical media storage device. Alternatively, the mass storage device may be implemented in an array of servers. Typically, the components of the computer system 1500 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1500 includes one or more input/output (I/O) devices and interfaces 1506, such as a keyboard, mouse, touch pad, and printer. The I/O devices and interfaces 1506 can include one or more display devices, such as a monitor, that allows the visual presentation of data to a user. More particularly, a display device provides for the presentation of GUIs as application software data, and multi-media presentations, for example. The I/O devices and interfaces 1506 can also provide a communications interface to the morcellator control unit 1516 or other various external devices. The computer system 1500 may include one or more multi-media devices 1504, such as speakers, video cards, graphics accelerators, and microphones, for example.

The computer system 1500 may run on a variety of computing devices, such as a server, a Windows server, and Structure Query Language server, a Unix Server, a personal computer, a laptop computer, and so forth. The computing system 1500 is generally controlled and coordinated by an operating system software, such as z/OS, Windows 95, Windows 98, Windows NT, Windows 2000, Windows XP, Windows Vista, Windows 7, Linux, BSD, SunOS, Solaris, or other compatible operating systems, including proprietary operating systems. Operating systems control and schedule computer processes for execution, perform memory management, provide file system, networking, and I/O services, and provide a user interface, such as a graphical user interface (GUI), among other things.

The output module may be implemented as a combination of an all-points addressable display such as a cathode ray tube (CRT), a liquid crystal display (LCD), a plasma display, or other types and/or combinations of displays. The output module may be implemented to communicate with input devices 1506 and they also include software with the appropriate interfaces which allow a user to access data through the use of stylized screen elements, such as menus, windows, dialogue boxes, tool bars, and controls (e.g., radio buttons, check boxes, sliding scales, and so forth). Furthermore, the output module may communicate with a set of input and output devices to receive signals from the user. The embodiments described above are intended to be merely exemplary and those skilled in the art shall be able to make numerous variations and modifications to it without departing from the spirit of the embodiments. All such variations and modifications are intended to be within the scope of the present invention as defined in the appended claims.

The methods and tasks described herein may often be performed and semi or fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the claims.

Although this invention has been disclosed in the context of certain preferred embodiments and examples, it will be understood by those skilled in the art that the scope of the claims extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above.

What is claimed is:

1. A processor-controlled tissue removal method, comprising:
   introducing an initial quantity of fluid into a body cavity in order to distend the body cavity;
   receiving a user-initiated signal to activate a tissue removal device having a distal working end disposed in the body cavity;
   in response to the received activation signal, and prior to activation of the tissue removal device, commencing introduction of an additional quantity of fluid into the body cavity; and
   activating the tissue removal device in order to remove tissue from the body cavity, wherein the tissue removal device is not activated until either (i) a predetermined time period has elapsed after commencing introduction of the additional quantity of fluid into the body cavity, or (ii) a predetermined elevated fluid pressure is reached within the body cavity due to the commenced introduction of the additional quantity of fluid.

2. The tissue removal method of claim 1, wherein the tissue removal device is activated after a predetermined time period has elapsed after commencing the introduction of the additional quantity of fluid into the body cavity.

3. The tissue removal method of claim 1, wherein the tissue removal device is activated after a predetermined elevated fluid pressure within the body cavity is reached due to the introduction of the additional quantity of fluid.

4. The tissue removal method of claim 1, wherein the body cavity is a uterus, and the tissue removed from the body cavity is uterine fibroid tissue.

5. A processor-controlled method for removing tissue from a body cavity using a tissue removal system, the tissue removal system comprising an introducer and a tissue removal device having a distal working end disposed in the body cavity, the method comprising:
   introducing fluid into the body cavity through the introducer until a desired fluid pressure level is reached in the body cavity;
   receiving, through a user activation switch, a signal to activate the tissue removal device;
   in response to the received activation signal, and prior to activation of the tissue removal device, activating a fluid pump to thereby introduce additional fluid into the body cavity through the introducer; and
   activating the tissue removal device in order to remove the tissue from the body cavity,
   wherein, in order to maintain the body cavity at least at the desired fluid pressure level, the additional fluid is introduced into the body cavity for a predetermined period before activating the tissue removal device, and
   wherein the predetermined period is based upon at least one of a time period threshold and a fluid pressure threshold.

6. The method of claim 5, further comprising, before activating the tissue removal device,
   analyzing the time period threshold and the fluid pressure threshold; and
   determining that one or both of the time period threshold and the pressure threshold has been satisfied.

7. The method of claim 5, wherein the predetermined period is based upon the time period threshold, such that the tissue removal device is not activated until additional fluid has been introduced into the body cavity for a predetermined amount of time.

8. The method of claim 5, wherein the predetermined period is based upon the fluid pressure threshold, such that the tissue removal device is not activated until a predetermined elevated fluid pressure level is reached in the body cavity due to the introduction of the additional fluid.

9. The method of claim 5, wherein the body cavity is a uterus, and the tissue removed from the body cavity is uterine fibroid material.

10. A processor-controlled method for removing fibroid tissue from a wall of a uterine cavity using a tissue removal system, the tissue removal system comprising an introducer having a working end in fluid communication with the uterine cavity, and a tissue removal device extending through the introducer and having a working distal end located in the uterine cavity, the method comprising:
    introducing fluid into the uterine cavity through the introducer to thereby distend the uterine cavity;
    receiving, through a user activation switch, a signal to activate the tissue removal device;
    in response to the received activation signal, and prior to activation of the tissue removal device, activating a fluid pump to thereby commence introduction of additional fluid into the uterine cavity through the introducer; and
    activating the tissue removal device in order to remove the tissue from the uterine cavity,
    wherein the tissue removal device is not activated until at least one of
    (i) a predetermined time period has elapsed after activating the fluid pump in response to the received activation signal, or
    (ii) a predetermined elevated fluid pressure is reached within the uterus cavity due to the commenced introduction of the additional quantity of fluid.

11. The fibroid tissue removal method of claim 10, wherein the tissue removal device is activated after a predetermined time period has elapsed following activation of the fluid pump in response to the received activation signal.

12. The tissue removal method of claim 10, wherein the tissue removal device is activated after a predetermined elevated fluid pressure is reached in the uterine cavity due to the introduction of the additional quantity of fluid.

13. The tissue removal method of claim 10, wherein after activating the tissue removal device, fluid is evacuated from the uterine cavity through the tissue removal device.

* * * * *